(12) United States Patent
Los et al.

(10) Patent No.: US 11,819,572 B2
(45) Date of Patent: Nov. 21, 2023

(54) TREATMENT OF PAIN BY ADMINISTRATION OF SUSTAINED-RELEASE LIPOSOMAL ANESTHETIC COMPOSITIONS

(71) Applicant: Pacira Pharmaceuticals, Inc., Parsippany, NJ (US)

(72) Inventors: Kathy Los, Parsippany, NJ (US); Vladimir Kharitonov, Parsippany, NJ (US)

(73) Assignee: Pacira Pharmaceuticals, Inc., Parsippany, NJ (US)

( * ) Notice: Subject to any disclaimer, the term of this patent is extended or adjusted under 35 U.S.C. 154(b) by 0 days.

(21) Appl. No.: 17/958,678

(22) Filed: Oct. 3, 2022

(65) Prior Publication Data

US 2023/0042662 A1    Feb. 9, 2023

Related U.S. Application Data

(63) Continuation of application No. 17/790,429, filed as application No. PCT/US2021/012269 on Jan. 6, 2021.

(60) Provisional application No. 63/064,760, filed on Aug. 12, 2020, provisional application No. 62/959,640, filed on Jan. 10, 2020.

(51) Int. Cl.
| | |
|---|---|
| *A61K 9/16* | (2006.01) |
| *A61K 9/127* | (2006.01) |
| *A61K 31/445* | (2006.01) |
| *A61K 31/485* | (2006.01) |
| *A61K 9/00* | (2006.01) |
| *A61K 47/02* | (2006.01) |
| *A61K 47/24* | (2006.01) |
| *A61K 47/26* | (2006.01) |

(52) U.S. Cl.
CPC ............ *A61K 9/127* (2013.01); *A61K 9/0019* (2013.01); *A61K 9/1277* (2013.01); *A61K 31/445* (2013.01); *A61K 31/485* (2013.01); *A61K 47/02* (2013.01); *A61K 47/24* (2013.01); *A61K 47/26* (2013.01)

(58) Field of Classification Search
CPC .......... A61K 9/14; A61K 9/141; A61K 9/143; A61K 9/145; A61K 9/16; A61K 9/1605; A61K 9/1611; A61K 9/48; A61K 9/4808; A61K 9/50; A61K 9/5089; A61K 9/51; A61K 9/5192
See application file for complete search history.

(56) References Cited

U.S. PATENT DOCUMENTS

| | | | |
|---|---|---|---|
| 5,316,771 A | 5/1994 | Barenholz | |
| 5,817,074 A | 10/1998 | Racz | |
| 8,182,835 B2 | 5/2012 | Kim et al. | |
| 8,410,104 B2 | 4/2013 | Brummett | |
| 8,834,921 B2 | 9/2014 | Kim et al. | |
| 8,906,966 B2 | 12/2014 | Sherwood et al. | |
| 8,957,779 B2 | 2/2015 | Wu et al. | |
| 8,975,268 B2 | 3/2015 | Berde et al. | |
| 8,975,281 B2 | 3/2015 | Berde et al. | |
| 9,192,575 B2 | 11/2015 | Kim et al. | |
| 9,205,052 B2 | 12/2015 | Kim et al. | |
| 9,585,838 B2 | 3/2017 | Hartounian et al. | |

(Continued)

FOREIGN PATENT DOCUMENTS

| | | |
|---|---|---|
| CN | 109745607 | 5/2019 |
| RU | 2307675 | 10/2007 |

(Continued)

OTHER PUBLICATIONS

Surdam et al (The Use of Exparel (Liposomal Bupivacaine) to Manage Postoperative Pain in Unilateral Total Knee Arthroplasty Patients; Journal of Arthroplasty 30, 2015, 325-329 (Year: 2015).*

(Continued)

*Primary Examiner* — Micah Paul Young
(74) *Attorney, Agent, or Firm* — Fish & Richardson P.C.

(57) ABSTRACT

In some embodiments provided herein is a method of treating pain, the method comprising administering into the subject
  a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  wherein inadvertent administration of the pharmaceutical composition into the vasculature of the subject does not result in cardiac side effects or CNS side effects in the subject.

30 Claims, No Drawings

(56) References Cited

U.S. PATENT DOCUMENTS

| | | |
|---|---|---|
| 10,398,648 B2 | 9/2019 | Schutt et al. |
| 2002/0039596 A1 | 4/2002 | Hartounian et al. |
| 2003/0059462 A1 | 3/2003 | Barenholz |
| 2003/0069318 A1 | 4/2003 | Dang et al. |
| 2003/0170288 A1 | 9/2003 | Carr et al. |
| 2006/0078606 A1 | 4/2006 | Kim et al. |
| 2007/0249681 A1 | 10/2007 | Sudo et al. |
| 2009/0105693 A1 | 4/2009 | Ben-David et al. |
| 2009/0202436 A1 | 8/2009 | Hobot et al. |
| 2011/0250264 A1 | 10/2011 | Schutt et al. |
| 2012/0179038 A1 | 6/2012 | Meurer et al. |
| 2013/0177633 A1 | 7/2013 | Schutt et al. |
| 2013/0177634 A1 | 7/2013 | Schutt et al. |
| 2013/0177635 A1 | 7/2013 | Schutt et al. |
| 2013/0177636 A1 | 7/2013 | Schutt et al. |
| 2013/0177637 A1 | 7/2013 | Schutt et al. |
| 2013/0177638 A1 | 7/2013 | Schutt et al. |
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0189349 A1 | 7/2013 | Kim et al. |
| 2013/0195965 A1 | 8/2013 | Schutt et al. |
| 2013/0306759 A1 | 11/2013 | Schutt et al. |
| 2013/0344132 A1 | 12/2013 | Kim et al. |
| 2014/0296293 A1 | 10/2014 | Andersen et al. |
| 2015/0250724 A1 | 9/2015 | Yamashita et al. |
| 2016/0000705 A1 | 1/2016 | McDonald et al. |
| 2016/0089335 A1 | 3/2016 | Ohri et al. |
| 2016/0361260 A1 | 12/2016 | Schutt et al. |
| 2016/0375140 A1 | 12/2016 | Ottoboni et al. |
| 2017/0007549 A1 | 1/2017 | Yum et al. |
| 2018/0092847 A1 | 4/2018 | Schutt et al. |
| 2019/0231762 A1 | 8/2019 | Verity |
| 2022/0015738 A1 | 1/2022 | Harbi et al. |
| 2022/0096116 A1 | 3/2022 | McFarland et al. |
| 2022/0273564 A1 | 5/2022 | Slonin et al. |
| 2022/0218613 A1 | 7/2022 | Slonin et al. |
| 2022/0387318 A1 | 12/2022 | Winston |
| 2023/0038098 A1 | 2/2023 | Winston et al. |
| 2023/0052319 A1 | 2/2023 | Winston et al. |
| 2023/0080593 A1 | 3/2023 | Winston et al. |
| 2023/0087140 A1 | 3/2023 | Winston et al. |

FOREIGN PATENT DOCUMENTS

| | | | |
|---|---|---|---|
| WO | WO 1997/003652 | 2/1997 | |
| WO | WO-9913865 A1 * | 3/1999 | ........... A61K 31/167 |
| WO | WO 1999/044640 | 9/1999 | |
| WO | WO 2016/174661 | 11/2016 | |
| WO | WO 2018/226732 | 12/2018 | |
| WO | WO 2018/237109 | 12/2018 | |
| WO | WO 2021/141956 | 7/2021 | |
| WO | WO 2021/141963 | 7/2021 | |

OTHER PUBLICATIONS

Hadzic et al (Liposome Bupivacaine Femoral Nerve Block for Postsurgical Analgesia after Total Knee Arthroplasty, Anesthesiology, V 124, No. 6 (Year: 2016).*

Tong et al (Liposomal bupivacaine and clinical outcomes; Best Practice & Research Clinical Anaesthesiology, 28, 15-17, 2014 (Year: 2014).*

Hadzic et al (Liposome Bupivacaine Femoral Nerve Block for Postsurgical Analgesia after Total Knee Arthosplasty. Anesthesop;pgy, V 124, No. 6 (Year: 2016).*

Tong et al (Liposomal bupivacaine and clinical outcomes; Best Practice & Research Clinical Anaesthesiology, 28, 15-17, 2014 (Year: 2014).*

Hadzic et al (Liposome Bupivacaine Femoral Nerve Block for Postsurgical Analgesia after Total Knee Arthroplasty. Anesthesop; pgy, V 124, No. 6 (Year: 2016).*

Rice et al (Pharmacokinetic Profile and Tolerability of Liposomal Bupivacine Following a Repeated Dose via Local Subcutaneous Infiltration in Healthy Volunteers; Clin Drug Investig, 2017, 37: 249-257) (Year: 2017).*

[No Author Listed] [online], "Full Prescribing Information—Exparel," exparel.com, revised Mar. 2022, retrieved on Apr. 14, 2022, retrieved from URL <https://www.exparel.com/hcp/prescribing-information.pdf?msclkid=60c82e5b2c231a2fdbe94c034f355fb2&utm_source=bing&utm_medium=cpc&utm_campaign=HCP%20-%20Branded&utm_term=exparel%20dosing%20information&utm_content=Dosage>, 36 pages.

Biotechnology Innovation Organization "Re: Docket No. FDA-2019-N-2514: Standards for Future Opioid Analgesic Approvals and Incentives for New Therapeutics to Treat Pain and Addiction," Nov. 18, 2019, 11 pages.

Delgado et al., "Validation of Digital Visual Analog Scale Pain Scoring With a Traditional Paper-based Visual Analog Scale in Adults," J Am Acad Orthop Surg Glob Res Rev., Mar. 2018, 2(3):e088, 6 pages.

Duzlu et al., "Release Pattern of Liposomal Bupivacaine in Artificial Cerebrospinal Fluid," Turk J Anaesth Reanim., 2016, 44:1-6.

FDA.gov [online] "Methodologies for Determining Opioid Sparing in Acute Pain Models," available on or before Dec. 14, 2019, via Internet Archive: Wayback Machine URL <http://web.archive.org/web/20191214114348/https://www.fda.gov/media/121206/download>, 61 pages.

Ginosar et al., "ED50 and ED95 of Intrathecal Hyperbaric Bupivacaine Coadministered with Opioids for Cesarean Delivery," Anesthesiology, Mar. 2004, 100(3):676-682.

Globalnewswire.com [online], "Pacira—EXPAREL Achieves Primary and Key Secondary Endpoints in Phase 4 CHOICE Study in Cesarean Section Patients," Jan. 7, 2020, retrieved on Apr. 11, 2022, retrieved from URL <https://www.globenewswire.com/news-release/2020/01/07/1967140/0/en/EXPAREL-Achieves-Primary-and-Key-Secondary-Endpoints-in-Phase-4-CHOICE-Study-in-Cesarean-Section-Patients.html>, 6 pages.

International Preliminary Report on Patentability in International Appln. No. PCT/US2021/012269, dated Jul. 21, 2022, 23 pages.

International Preliminary Report on Patentability in International Appln. No. PCT/US2021/012275, dated Jul. 12, 2022, 13 pages.

International Preliminary Report on Patentability in International Appln. No. PCT/US2021-012266, dated Jul. 12, 2022, 14 pages.

International Search Report and Written Opinion in International Appln. No. PCT/US2021/012266, dated Apr. 30, 2021, 16 pages.

International Search Report and Written Opinion in International Appln. No. PCT/US2021/012269, dated Mar. 25, 2021, 25 pages.

International Search Report and Written Opinion in International Appln. No. PCT/US2021/012275, dated Mar. 25, 2021, 14 pages.

Joshi et al., "The Safety of Liposome Bupivacaine Following Various Routes of Administration in Animals," Journal of Pain Research, 2015, 8:781-789.

Kim et al., "Preparation of multivesicular liposomes," Biochim. Biophys. Acta—Biomembranes, Mar. 9, 1983, 728(3):339-348.

Laura Giron-Arango et al., "Pericapsular Nerve Group (PENG) Block for Hip Fracture", Reg Anesth Pain Med, 2018, 43:859-863, 5 pages.

Malik et al., "Emerging Roles of Liposomal Bupivacaine in Anesthesia Practice," Journal of Anaesthesiology Clinical Pharmacology, Apr.-Jun. 2017, 33(2):151-156.

Malinovsky et al., "Neurotoxicological Assessment After Intracisternal Injection of Liposomal Bupivacaine in Rabbits," Anesth. Analg., 1997, 85:1331-1336.

Nedeljkovic et al., "Liposomal Bupivacaine Transversus Abdominis Plane Block for Pain After Cesarean Delivery: Results From a Multicenter, Randomized, Double-Blind, Controlled Trial," PowerPoint, Presented at Society for Obstetric Anesthesia and Perinatology 51st Annual Meeting, Phoenix, AZ, May 1-5, 2019, 17 pages.

Nedeljkovic et al., "Transversus Abdominis Plane Block With Liposomal Bupivacaine for Pain After Cesarean Delivery in a Multicenter, Randomized, Double-Blind, Controlled Trial," Anesth. Analg., Dec. 2020, 131(6):1830-1839.

Patel et al., "Brachial Plexus Block with Liposomal Bupivacaine for Shoulder Surgery Improves Analgesia and Reduces Opioid Con-

(56) References Cited

OTHER PUBLICATIONS sumption: Results from a Multicenter, Randomized, Double-Blind, Controlled Trial," Pain Medicine, 2019, 21(2):387-400, 14 pages.

Perets et al., "Intraoperative Infiltration of Liposomal Bupivacaine vs Bupivacaine Hydrochloride for Pain Management in Primary Total Hip Arthroplasty: A Prospective Randomized Trial," The Journal of Arthroplasty, 2018, 33:441-446.

Scott et al., "Acute Toxicity of Ropivacaine Compared with that of Bupivacaine," Anesthesia and Analgesia, Nov. 1, 1989, 69(5):563-569.

www.sec.gov [online], "Pacira BioSciences Reports First Quarter 2019 Revenues of $91.3 Million," May 2019, retrieved on Sep. 30, 2022, retrieved from URL <https://www.sec.gov/Archives/edgar/data/1396814/000139681419000012/pcrx-3312019x991.htm>, 12 pages.

Zel et al., "Neurological and Histological Outcomes After Subarachnoid Injection of a Liposomal Bupivacaine Suspension in Pigs: A Pilot Study," British Journal of Anaesthesia, Mar. 2019, 122(3):379-387.

[No Author Listed] [online], "Highlights of Prescribing Information—EXPAREL," accessdata.fda.gov, Apr. 2018, retrieved on Jun. 17, 2022, retrieved from URL <www.accessdata.fda.gov/drugsatfda_docs/label/2018/022496s9lbl.pdf>, 28 pages.

[No Author Listed] [online], "Marcaine [package insert]," accessdata.fda.gov, Oct. 2011, retrieved on Jun. 21, 2022, retrieved from URL <https://www.accessdata.fda.gov/drugsatfda_docs/label/2012/018692s015lbl.pdf>, 30 pages.

[No Author Listed] [online], "Naropin [package insert]," accessdata.fda.gov, Nov. 2018, retrieved on Jun. 21, 2022, retrieved from URL <https://www.accessdata.fda.gov/drugsatfda_docs/label/2018/020533s035lbl.pdf>, 30 pages.

Ahiskalioglu et al., "Can high volume pericapsular nerve group (PENG) block act as a lumbar plexus block?" Journal of Clinical Anesthesia, May 2020, 61:109650, 2 pages.

American Society of Anesthesiologists Task Force on Acute Pain Management, "Practice guidelines for acute pain management in the perioperative setting: an updated report by the American Society of Anesthesiologists Task Force on Acute Pain Management," Anesthesiology, Feb. 2012, 116(2):248-273.

American Society of Anesthesiologists, "ASA Physical Status Classification System," asahq.org, Dec. 13, 2020, retrieved from URL <https://www.asahq.org/standards-and-guidelines/asa-physical-status-classification-system>, 4 pages.

Beachler et al. "Liposomal bupivacaine in total hip arthroplasty: Do the results justify the cost?" Journal of Orthopaedics, 2017, 14:161-165.

Bigeleisen et al., "Novel approaches in pain management in cardiac surgery," Curr Opin Anaesthesiol. Feb. 2015, 28(1):89-94.

Bronson et al. "Unanticipated transient sciatic nerve deficits from intra-wound liposomal bupivacaine injection during total hip arthroplasty," Arthroplasty Today, 2015, 1:21-24.

Chughtai et al., "Liposomal Bupivacaine Is Both Safe and Effective in Controlling Postoperative Pain After Spinal Surgery in Children: A Controlled Cohort Study," Clin Spine Surg., 2020, 33(10):E533-E538.

Cohen et al., "Incidence of adverse events attributable to bupivacaine liposome injectable suspension or plain bupivacaine for postoperative pain in pediatric surgical patients: A retrospective matched cohort analysis," Paediatr Anaesth., 2019, 29(2):169-174, 15 pages.

Day et al., "Extended Release Liposomal Bupivacaine Injection (Exparel) for Early Postoperative Pain Control Following Pharyngoplasty," J Craniofac Surg., Jul. 2018, 29(3):726-730, 4 pages.

De Leeuw et al., "The Psoas Compartment Block for Hip Surgery: The Past, Present, and Future," Anesthesiology Research and Practice, 2011, Article ID 159541, pp. 1-6.

Ecoffey, "Refresher course: Local anesthetic pharmacology in children," Regional Anesthesia and Pain Medicine, 2015, 40(5):e23-e25.

Gan, "Poorly controlled postoperative pain: prevalence, consequences, and prevention," J Pain Res. 2017, 10:2287-2298.

Gerbershagen et al., "Pain intensity on the first day after surgery: a prospective cohort study comparing 179 surgical procedures," Anesthesiology, Apr. 2013, 118(4):934-944.

Giron Arango et al., "Reply to Dr Yu et al.: Inadvertent quadriceps weakness following the pericapsular nerve group (PENG) block," Reg Anesth Pain Med, May 2019, 44(5):613-614.

Gottschalk et al., "Quality of postoperative pain using an intraoperatively placed epidural catheter after major lumbar spinal surgery," Anesthesiology, Jul. 2004, 101(1):175-180.

Hu et al., "Pharmacokinetic profile of liposome bupivacaine injection following a single administration at the surgical site," Clin Drug Investig., 2013, 33(2):109-115.

International Search Report and Written Opinion in International Appln. No. PCT/US2022/011828, dated Apr. 1, 2022, 18 pages.

International Search Report and Written Opinion in International Appln. No. PCT/US2022/020713, dated Jun. 14, 2022, 24 pages.

Li et al., "Acute postoperative opioid consumption trajectories and long-term outcomes in pediatric patients after spine surgery," J Pain Res., 2019, 12:1673-1684.

Manna et al., "Probing the mechanism of bupivacaine drug release from multivesicular liposomes," J Control Release, Jan. 28, 2019, 294:279-287, 41 pages.

Mannion et al., "In with the New, Out with the Old? Comparison of Two Approaches for Psoas Compartment Block," Anesthesia and Analgesia, 2005, 101:259-264.

Mannion, "Psoas Compartment Block," Continuing Education in Anesthesia, Critical Care & Pain, 2007, 7(5):162-166.

Mazoit et al., "Pharmacokinetics of bupivacaine following caudal anesthesia in infants," Anesthesiology, Mar. 1, 1988, 68(3):387-391.

McGraw-Tatum et al. "A Prospective, Randomized Trial Comparing Liposomal Bupivacaine vs Fascia Iliaca Compartment Block for Postoperative Pain Control in Total Hip Arthroplasty," The Journal of Arthroplasty, 2017, 32:2181-2185.

Oda, "Pharmacokinetics and systemic toxicity of local anesthetics in children," Journal of anesthesia, Jun. 16, 2016, 30(4):547-550.

Peng et al., "Reply to Dr Nielsen: Pericapsular Nerve Group (PENG) block for hip fracture," Reg Anesth Pain Med, Mar. 2019, 44(3):415-416.

Rabbitts et al., "Presurgical psychosocial predictors of acute post-surgical pain and quality of life in children undergoing major surgery," J Pain., Mar. 2015, 16(3):226-234.

Rabbitts et al., "Trajectories of postsurgical pain in children: risk factors and impact of late pain recovery on long-term health outcomes after major surgery," Pain, Nov. 2015, 156(11):2383-2389.

Raja et al., "The revised International Association for the Study of Pain definition of pain: concepts, challenges, and compromises," PAIN, Sep. 1, 2020, 161(9):1976-1982.

Rice et al., "Pharmacokinetic Profile and Tolerability of Liposomal Bupivacaine Following a Repeated Dose via Local Subcutaneous Infiltration in Healthy Volunteers," Clin Drug Investig., 2017, 37(3):249-257.

Santos et al., "Is Continuous PENG Block the New 3-in-1?" J Anesth Clin Res 2019, Jun. 28, 2019, 10(6): 1000898, 2 pages.

Shah et al., "Current Trends in Pediatric Spine Deformity Surgery: Multimodal Pain Management and Rapid Recovery," Global Spine J., 2020, 10(3):346-352.

Short et al., "Anatomic Study of Innervation of the Anterior Hip Capsule: Implication for Image-Guided Intervention," Regional Anesthesia and Pain Medicine, Feb. 2018, 43(2):186-192.

Springer et al., "Systemic Safety of Liposomal Bupivacaine in Simultaneous Bilateral Total Knee Arthroplasty," J Arthroplasty., Jan. 2018, 33(1):97-101.

Therapy Services Patient Information [online] "Pubic Rami Fracture," retrieved on Jan. 11, 2023, retrieved from URL <https://www.uhd.nhs.uk/uploads/about/docs/our_publications/patient_information_leaflets/orthopaedics/Pubic_rami_fracture.pdf>, 12 pages.

Tirotta et al., "Continuous incisional infusion of local anesthetic in pediatric patients following open heart surgery," Pediatr Anaesth., Jun. 2009, 19(6):571-576.

Tran et al.., "Is pericapsular nerve group (PENG) block a true pericapsular block?," Reg Anesth Pain Med, Feb. 2019, 44(2):257.

(56) References Cited

OTHER PUBLICATIONS

USFaD, "Pediatric Study Plans: Content of and Process for Submitting Initial Pediatric Study Plans and Ameded Initial Pediatric Study Plans Guidance for Industry," US Food and Drug Administration, Jul. 2020, retrieved from URL <https://www.fda.gov/media/86340/download>, 26 pages.
Walker et al., "Complications in Pediatric Regional Anesthesia: An Analysis of More than 100,000 Blocks from the Pediatric Regional Anesthesia Network," Anesthesiology, Oct. 2018, 129(4):721-732.
Yu et al., "Inadvertent quadriceps weakness following the pericapsular nerve group (PENG) block," Reg Anesth Pain Med, May 2019, 44(5):611-613.
Domb et al., "The effect of liposomal bupivacaine injection during total hip arthroplasty: a controlled cohort study," BMC Musculosketeal Disorders, 2014, 15(310):1-6.
[No Author Listed] [online], "Adductor Canal Block," RAUKvideos, uploaded on Jan. 29, 2021, retrieved on May 25, 2023, retrieved from URL <https://www.youtube.com/watch?v=DZLjNHkbMtI>, 2 pages [Video Submission].
[No Author Listed] [online], "Adductor Canal Block: What Nerves Are We After?," Regional Anesthesiology and Acute Pain Medicine, uploaded on Oct. 2, 2020, retrieved from internet on May 25, 2023, retrieved from URL <https://www.youtube.com/watch?v=fE4U7JQa2f8>, 2 pages [ Video Submission].
Acharya et al., "Pericapsular Nerve Group Block: An Excellent Option for Analgesia for Positional Pain in Hip Fractures," Case Reports in Anesthesiology, Mar. 12, 2020, 2020,(1830136):1-3.
Ackmann et al., "Anatomy of the Infrapatellar Branch in Relation to Skin Incisions and as the Basis to Treat Neuropathic Pain by Percutaneous Cryodenervation," Pain Physician Journal, May/Jun. 2014, 17:E229-E348.
Bagaria et al., "The feasibility of direct adductor canal block (DACB) as a part of periarticular injection in total knee arthroplasty," Knee Surgery & Related Research, 2020, 32(48), 7 pages.
Chin et al., "Mechanisms of action of fascial plane blocks: a narrative review," Regional Anesthesia and Pain Medicine, 2021, 46:618-628.
Fiol et al., "Is There a Role for Liposomal Bupivacaine as Part of a Multimodal Strategy Inclusive of Intrathecal Morphine for Post-Cesarean Analgesia? A Retrospective Chart Review Study," Anesth. Pain Res., 2020, 4(2):1-6.
Greenky et al., "Intraoperative Surgeon Administered Adductor Canal Blockade Is Not Inferior to Anesthesiologist Administered Adductor Canal Blockade: A Prospective Randomized Trial," The Journal of Arthroplasty, 2020, 35:1228-1232.
International Preliminary Report on Patentability in International Appln. No. PCT/US2022/011828, dated Jul. 20, 2023, 16 pages.
Li et al., "Ultrasound-guided single popliteal sciatic nerve block is an effective postoperative analgesia strategy for calcaneal fracture: a randomized clinical trial," BMC Musculoskeletal Disorders, Jan. 2021, 22(735):1-9.
Matthews et al., "Surgeon-placed peripheral nerve block and continuous non-opioid analgesia in total knee arthroplasty is accessible intraoperatively: A cadaveric study," Journal of ISAKOS, Mar. 2023, 6 pages.
Matthews, "Continuous Adductor Canal & Periarticular Nerve Block for Total Knee Arthroplasty, Matthews' Placement Guide," Surgical Solutions, 2021, 6 pages.
MayfieldClinic.com [online], "Epidural Steroid Injections (ESI)," Mayfield Brain & Spine, Jul. 2018, retrieved on May 9, 2023, retrieved from URL <https://d3djccaurgtij4.cloudfront.net/pe-esi.pdf>, 3 pages.
Mont et al., "Can Joint Arthroplasty Surgeons Safely Administer Anesthesia?," The Journal of Arthroplasty, 2020, 35:1169.
Pepper et al., "Intraoperative Adductor Canal Block for Augmentation of Periarticular Injection in Total Knee Arthroplasty: A Cadaveric Study," The Journal of Arthroplasty, 2016, 31:2072-2076.
Peterson et al., "Surgeon-Performed High-Dose Bupivacaine Periarticular Injection with Intra-Articular Saphenous Nerve Block is Not Inferior to Adductor Canal Block in Total Knee Arthroplasty," The Journal of Arthroplasty, May 2020, 35:1233-1238.
Rongstad et al., "Popliteal Sciatic Nerve Block for Postoperative Analgesia," Foot & Ankle International, Jul. 1996, 17(7):378-382.
Runge et al., "The Spread of Ultrasound-Guided Injectate From the Adductor Canal to the Genicular Branch of the Posterior Obturator Nerve and the Popliteal," Regional Anesthesia and Acute Pain, Dec. 2017, 42(6):725-730.
Sveom et al., "Ultrasound-Guided Adductor Canal Block Versus Intraoperative Transarticular Saphenous Nerve Block: A Retrospective Analysis," The Journal of Arthroplasty, 2022, 37:S134-S138.
Tak et al., "Continuous adductor canal block is superior to adductor canal block alone or adductor canal block combined with IPACK block (interspace between the popliteal artery and the posterior capsule of knee) in postoperative analgesia and ambulation following continued from U): total knee arthroplasty: randomized control trial," Musculoskeletal Surg., Jun. 2022, 106:155-162.
Teachmeanatomy.info [online], "Anatomical Planes," Sep. 30, 2022, retrieved on Jun. 13, 2023, retrieved from URL <https://teachmeanatomy.info/the-basics/anatomical-terminology/planes/>, 2 pages.
Tran et al., "Evaluation of the proximal adductor canal block injectate spread: a cadaveric study," Reg. Anesth. Pain. Med., 2020, 45:124-130.
Worrell et al., "The Mayo block: an efficacious block for hallux and first metatarsal surgery," AANA Journal, Apr. 1, 1996, 64(2):146-152, Abstract only.
Yee et al., "Quadriceps Weakness After Single-Short Adductor Canal Block," The Journal of Bone and Joint Surgery, 2021, 103(1):30-36.

* cited by examiner

TREATMENT OF PAIN BY ADMINISTRATION OF SUSTAINED-RELEASE LIPOSOMAL ANESTHETIC COMPOSITIONS

CROSS-REFERENCE TO RELATED APPLICATIONS

This application is a continuation of U.S. application Ser. No. 17/790,429, filed Jun. 30, 2022, which is a National Stage application under 35 U.S.C. § 371 of International Application No. PCT/US2021/012269, filed Jan. 6, 2021, which claims the benefit of U.S. Provisional Application Ser. No. 62/959,640, filed Jan. 10, 2020, and U.S. Provisional Application Ser. No. 63/064,760, filed Aug. 12, 2020, each of which is incorporated by reference herein in its entirety.

BACKGROUND

Local anesthetics can have toxic effects when injected intravenously (i.e. local anesthetic systemic toxicity, or LAST). Initial CNS symptoms can occur even at low intravenous doses. Later symptoms including serious CNS dysfunction and cardiovascular effects can be severe and life-threatening. Patient reports of early mild symptoms can be utilized to determine when a local anesthetic dose is intolerable, before serum levels reach a point at which serious toxicity will occur.

There continues to be a need for methods of treating pain in a subject or of anesthetizing a subject, that are both effective and safe in the event of an inadvertent intravascular injection of the anesthetic or analgesic

SUMMARY

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
  wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome,
  wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject does not result in cardiac side effects or CNS side effects in the subject.

In some embodiments, the method of treating pain in a subject comprises administering an opioid to the subject following the administration of the pharmaceutical composition.

In some embodiments, the opioid is administered in a total amount less than 50 mg in the first about 72 hours following the administration of the pharmaceutical composition.

In some embodiments provided herein is a method of treating pain in a subject, the method comprising administering into the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein the plasma Cmax of bupivacaine in the subject following the administering of the pharmaceutical composition is lower than the plasma Cmax of bupivacaine in the subject following administration to the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject an amount of a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein the plasma Cmax of bupivacaine in the subject following the administering of the pharmaceutical composition is lower than the plasma Cmax of bupivacaine in the subject following administration to the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject an amount of a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, wherein the plasma Cmax of bupivacaine in the subject following the administering of the pharmaceutical composition is lower than the plasma Cmax of bupivacaine in the subject following administration to the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein the plasma Cmax of bupivacaine in the subject following the administering of the pharmaceutical composition is lower than the plasma Cmax of bupivacaine in the subject following administration to the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein the plasma Cmax of bupivacaine in the subject following the administering of the pharmaceutical composition is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject an amount of a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein the plasma Cmax of bupivacaine in the subject following the administering of the pharmaceutical composition is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject an amount of a pharmaceutical composition comprising multivesicular liposomes encapsulating bupivacaine phosphate, said multivesicular liposomes comprising bupivacaine or a salt thereof;

phosphoric acid;

a lipid component comprising at least one amphipathic lipid and at least one neutral lipid lacking a hydrophilic head group; and, optionally, a cholesterol and/or a plant sterol wherein said multivesicular liposomes are made by a process comprising:

a) preparing a first aqueous component comprising phosphoric acid;

b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, wherein the plasma Cmax of bupivacaine in the subject following the administering of the pharmaceutical composition is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
    wherein the plasma Cmax of bupivacaine in the subject following the administering of the pharmaceutical composition is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject an amount of a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
    wherein the plasma Cmax of bupivacaine in the subject following the administering of the pharmaceutical composition is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject an amount of a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
    wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
    wherein the plasma Cmax of bupivacaine in the subject following the administering of the pharmaceutical composition is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments, the plasma Cmax of bupivacaine in the subject following the administering of the pharmaceutical composition is from about 2 times to about 4 times less than the plasma Cmax of bupivacaine in the subject following administration to the subject of the non-liposomal bupivacaine.

In some embodiments, the plasma Cmax of bupivacaine in the subject following the administering of the pharmaceutical composition is from about 2 times to about 4 times less than the plasma Cmax of bupivacaine in the subject that would result from administration to the subject of the non-liposomal bupivacaine.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
    wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and, optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
   wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
   wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
   wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
   wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
   wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a pharmaceutical composition comprising multivesicular liposomes encapsulating bupivacaine phosphate, said multivesicular liposomes comprising
   bupivacaine or a salt thereof;
   phosphoric acid;
   a lipid component comprising at least one amphipathic lipid and at least one neutral lipid lacking a hydrophilic head group; and,
   optionally, a cholesterol and/or a plant sterol wherein said multivesicular liposomes are made by a process comprising:
   a) preparing a first aqueous component comprising phosphoric acid;
   b) preparing a lipid component comprising at least one organic solvent, at least one amphipathic lipid, and at least one neutral lipid lacking a hydrophilic head group;
   c) mixing said first aqueous component and said lipid component to form a water-in-oil emulsion, wherein at least one component comprises bupivacaine or a salt thereof;
   d) mixing said water-in-oil emulsion with a second aqueous component to form solvent spherules; and
   e) removing the organic solvent from the solvent spherules to form multivesicular liposomes encapsulating bupivacaine phosphate,
   wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:

a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
    wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
    wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
    wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
    wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
    wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a pharmaceutical composition comprising multivesicular liposomes encapsulating bupivacaine phosphate, said multivesicular liposomes comprising
    bupivacaine or a salt thereof;
    phosphoric acid;
    a lipid component comprising at least one amphipathic lipid and at least one neutral lipid lacking a hydrophilic head group; and,
    optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate,
    wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments, the method does not comprise administering the pharmaceutical composition by intravenous injection.

In some embodiments, the pharmaceutical composition is administered into the subject in proximity to a wound in the subject.

DETAILED DESCRIPTION

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
    wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a pharmaceutical composition comprising multivesicular liposomes encapsulating bupivacaine phosphate, said multivesicular liposomes comprising
    bupivacaine or a salt thereof;
    phosphoric acid;
    a lipid component comprising at least one amphipathic lipid and at least one neutral lipid lacking a hydrophilic head group; and,
    optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate,
    wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
    wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
    wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by infiltration a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by infiltration a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by interscalene brachial plexus nerve block a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by interscalene brachial plexus nerve block a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel;

applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a pharmaceutical composition comprising multivesicular liposomes encapsulating bupivacaine phosphate, said multivesicular liposomes comprising bupivacaine or a salt thereof;
    phosphoric acid;
    a lipid component comprising at least one amphipathic lipid and at least one neutral lipid lacking a hydrophilic head group; and,
    optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by transversus abdominis plane (TAP) block a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by transversus abdominis plane (TAP) block a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject by subarachnoid injection a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject. In some embodiments provided herein is a method of treating pain in a subject, the method comprising administering into the subject by subarachnoid injection a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject by subarachnoid injection a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments, the method does not comprise administering the pharmaceutical composition by intravenous injection.

In some embodiments, the pharmaceutical composition is administered into the subject in proximity to a wound in the subject.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject does not result in at least one or more of the cardiac side effects or CNS side effects in the subject that result or would result from inadvertent administration of a non-liposomal bupivacaine containing the same amount of bupivacaine as the pharmaceutical composition. For example, the cardiac side effects or CNS side effects may result following inadvertent injection of the non-liposomal bupivacaine into the vasculature of a second subject in proximity to a wound in the second subject.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject does not result in at least one or more of the cardiac side effects or CNS side effects in the subject that result or would result from inadvertent administration of a non-liposomal bupivacaine containing the same amount of bupivacaine as the pharmaceutical composition.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate, wherein inadvertent administration of the pharmaceutical composition into the vasculature of the subject does not result in at least one or more of the cardiac side effects or CNS side effects in the subject that result or would result from inadvertent administration of a non-liposomal bupivacaine containing the same amount of bupivacaine as the pharmaceutical composition.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject does not result in at least one or more of the cardiac side effects or CNS side effects in the subject that result or would result from inadvertent administration of a non-liposomal bupivacaine containing the same amount of bupivacaine as the pharmaceutical composition.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject does not result in at least one or more of the cardiac side effects or CNS side effects in the subject that result or would result from inadvertent administration of a non-liposomal bupivacaine containing the same amount of bupivacaine as the pharmaceutical composition.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject does not result in at least one or more of the cardiac side effects or CNS side effects in the subject that result or would result from inadvertent administration of a non-liposomal bupivacaine containing the same amount of bupivacaine as the pharmaceutical composition.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject following inadvertent administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject following inadvertent administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate, wherein inadvertent administration of the pharmaceutical composition into the vasculature of the subject provides a plasma Cmax of bupivacaine that is lower than the plasma Cmax of bupivacaine in the subject following inadvertent administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject provides a plasma Cmax of bupivacaine that is lower than the plasma Cmax of bupivacaine in the subject following inadvertent administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject provides a plasma Cmax of bupivacaine that is lower than the plasma Cmax of bupivacaine in the subject following inadvertent administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject provides a plasma Cmax of bupivacaine that is lower than the plasma Cmax of bupivacaine in the subject following inadvertent administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject results in less severe cardiac side effects or CNS side effects in the subject as compared to those observed following inadvertent administration into the vasculature of non-liposomal bupivacaine containing the same amount of bupivacaine as the pharmaceutical composition. For example, the cardiac side effects or CNS side effects may result following inadvertent injection of the non-liposomal bupivacaine into the vasculature of a second subject in proximity to a wound in the second subject.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject results in less severe cardiac side effects or CNS side effects in the subject as compared to those observed following inadvertent administration into the vasculature of non-liposomal bupivacaine containing the same amount of bupivacaine as the pharmaceutical composition. In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and, optionally, a cholesterol and/or a plant sterol wherein said multivesicular liposomes are made by a process comprising:

a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate, wherein inadvertent administration of the pharmaceutical composition into the vasculature of the subject results in less severe cardiac side effects or CNS side effects in the subject as compared to those observed following inadvertent administration into the vasculature of non-liposomal bupivacaine containing the same amount of bupivacaine as the pharmaceutical composition.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein the aqueous phase is encapsulated within the multivesicular liposome, wherein inadvertent administration of the pharmaceutical composition into the vasculature of the subject results in less severe cardiac side effects or CNS side effects in the subject as compared to those observed following inadvertent administration into the vasculature of non-liposomal bupivacaine containing the same amount of bupivacaine as the pharmaceutical composition.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject results in less severe cardiac side effects or CNS side effects in the subject as compared to those that would result from inadvertent administration into the vasculature of non-liposomal bupivacaine containing the same amount of bupivacaine as the pharmaceutical composition. For example, the cardiac side effects or CNS side effects could result following inadvertent injection of the non-liposomal bupivacaine into the vasculature of a second subject in proximity to a wound in the second subject.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject results in less severe cardiac side effects or CNS side effects in the subject as compared to those that would result from inadvertent administration into the vasculature of non-liposomal bupivacaine containing the same amount of bupivacaine as the pharmaceutical composition.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate, wherein inadvertent administration of the pharmaceutical composition into the vasculature of the subject results in less severe cardiac side effects or CNS side effects in the subject as compared to those that would result from inadvertent administration into the vasculature of non-liposomal bupivacaine containing the same amount of bupivacaine as the pharmaceutical composition.

In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
  wherein inadvertent administration of the pharmaceutical composition into the vasculature of the subject results in less severe cardiac side effects or CNS side effects in the subject as compared to those that would result from inadvertent administration into the vasculature of non-liposomal bupivacaine containing the same amount of bupivacaine as the pharmaceutical composition.

In some embodiments provided herein is a method of treating pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
  wherein inadvertent administration of the pharmaceutical composition into the vasculature of the subject results in less severe cardiac side effects or CNS side effects in the subject as compared to those that would result from inadvertent administration into the vasculature of non-liposomal bupivacaine containing the same amount of bupivacaine as the pharmaceutical composition.

In some embodiments provided herein is a method of treating pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
  wherein inadvertent administration of the pharmaceutical composition into the vasculature of the subject results in less severe cardiac side effects or CNS side effects in the subject as compared to those that would result from inadvertent administration into the vasculature of non-liposomal bupivacaine containing the same amount of bupivacaine as the pharmaceutical composition.

In some embodiments provided herein is a method of treating pain in a subject, the method comprising:
  A) administering into the subject in a first time period in proximity to a wound in the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
  B) determining that inadvertent administration of the pharmaceutical composition into the vasculature of the subject has occurred;
  C) if the inadvertent administration of the pharmaceutical composition in step B) is determined to have occurred, monitoring the subject for cardiac side effects and CNS side effects;

and
D) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of treating pain in a subject, the method comprising:
a) administering into the subject in a first time period in proximity to a wound in the subject an amount of a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
b) determining that inadvertent administration of the pharmaceutical composition into the vasculature of the subject has occurred;
c) if the inadvertent administration of the pharmaceutical composition in step b) is determined to have occurred, monitoring the subject for cardiac side effects and CNS side effects; and
d) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step a).

In some embodiments provided herein is a method of treating pain in a subject, the method comprising:
A) administering into the subject in a first time period in proximity to a wound in the subject an amount of a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.
B) determining that inadvertent administration of the pharmaceutical composition into the vasculature of the subject has occurred;
C) if the inadvertent administration of the pharmaceutical composition in step B) is determined to have occurred, monitoring the subject for cardiac side effects and CNS side effects; and
D) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of treating pain in a subject, the method comprising:
A) administering into the subject in a first time period in proximity to a wound in the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
B) determining that inadvertent administration of the pharmaceutical composition into the vasculature of the subject has occurred;
C) if the inadvertent administration of the pharmaceutical composition in step B) is determined to have occurred, monitoring the subject for cardiac side effects and CNS side effects; and
D) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of treating pain in a subject, the method comprising:
A) administering into the subject in a first time period in proximity to a wound in the subject an amount of a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, B) determining that inadvertent administration of the pharmaceutical composition into the vasculature of the subject has occurred;

C) if the inadvertent administration of the pharmaceutical composition in step B) is determined to have occurred, monitoring the subject for cardiac side effects and CNS side effects;

and

D) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of treating pain in a subject, the method comprising:

A) administering into the subject in a first time period in proximity to a wound in the subject an amount of a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, B) determining that inadvertent administration of the pharmaceutical composition into the vasculature of the subject has occurred;

C) if the inadvertent administration of the pharmaceutical composition in step B) is determined to have occurred, monitoring the subject for cardiac side effects and CNS side effects;

and

D) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of treating pain in a subject, the method comprising:

A) administering into the subject in a first time period in proximity to a wound in the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, B) determining that inadvertent administration of the pharmaceutical composition into the vasculature of the subject has occurred; and C) if the inadvertent administration of the pharmaceutical composition in step B) is determined to have occurred, monitoring the plasma level of bupivacaine in the subject.

In some embodiments provided herein is a method of treating pain in a subject, the method comprising:

a) administering into the subject in a first time period in proximity to a wound in the subject an amount of a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, b) determining that inadvertent administration of the pharmaceutical composition into the vasculature of the subject has occurred; and c) if the inadvertent administration of the pharmaceutical composition in step b) is determined to have occurred, monitoring the plasma level of bupivacaine in the subject.

In some embodiments provided herein is a method of treating pain in a subject, the method comprising:

A) administering into the subject in a first time period in proximity to a wound in the subject an amount of a pharmaceutical composition comprising multivesicular liposomes encapsulating bupivacaine phosphate, said multivesicular liposomes comprising bupivacaine or a salt thereof;

phosphoric acid;

a lipid component comprising at least one amphipathic lipid and at least one neutral lipid lacking a hydrophilic head group; and, optionally, a cholesterol and/or a plant sterol wherein said multivesicular liposomes are made by a process comprising:

a) preparing a first aqueous component comprising phosphoric acid;

b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, B) determining that inadvertent administration of the pharmaceutical composition into the vasculature of the subject has occurred; and C) if the inadvertent administration of the pharmaceutical composition in step B) is determined to have occurred, monitoring the plasma level of bupivacaine in the subject.

In some embodiments provided herein is a method of treating pain in a subject, the method comprising:

A) administering into the subject in a first time period in proximity to a wound in the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, B) determining that inadvertent administration of the pharmaceutical composition into the vasculature of the subject has occurred; and C) if the inadvertent administration of the pharmaceutical composition in step B) is determined to have occurred, monitoring the plasma level of bupivacaine in the subject.

In some embodiments provided herein is a method of treating pain in a subject, the method comprising:

A) administering into the subject in a first time period in proximity to a wound in the subject an amount of a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, B) determining that inadvertent administration of the pharmaceutical composition into the vasculature of the subject has occurred; and C) if the inadvertent administration of the pharmaceutical composition in step B) is determined to have occurred, monitoring the plasma level of bupivacaine in the subject.

In some embodiments provided herein is a method of treating pain in a subject, the method comprising:

A) administering into the subject in a first time period in proximity to a wound in the subject an amount of a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, B) determining that inadvertent administration of the pharmaceutical composition into the vasculature of the subject has occurred; and C) if the inadvertent administration of the pharmaceutical composition in step B) is determined to have occurred, monitoring the plasma level of bupivacaine in the subject.

In some embodiments provided herein is a method of treating pain in a subject, the method comprising:

A) administering into the subject in a first time period in proximity to a wound in the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, B) monitoring the subject for cardiac side effects and CNS side effects following any inadvertent administration of the pharmaceutical composition into the vasculature of the subject;

and

C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of treating pain in a subject, the method comprising:

a) administering into the subject in a first time period in proximity to a wound in the subject an amount of a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, b) monitoring the subject for cardiac side effects and CNS side effects following any inadvertent administration of the pharmaceutical composition into the vasculature of the subject; and c) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step a).

In some embodiments provided herein is a method of treating pain in a subject, the method comprising:

A) administering into the subject in a first time period in proximity to a wound in the subject an amount of a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:

a) preparing a first aqueous component comprising phosphoric acid;

b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, B) monitoring the subject for cardiac side effects and CNS side effects following any inadvertent administration of the pharmaceutical composition into the vasculature of the subject;

and

C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of treating pain in a subject, the method comprising:

A) administering into the subject in a first time period in proximity to a wound in the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, B) monitoring the subject for cardiac side effects and CNS side effects following any inadvertent administration of the pharmaceutical composition into the vasculature of the subject; and C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of treating pain in a subject, the method comprising:

A) administering into the subject in a first time period in proximity to a wound in the subject an amount of a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, B) monitoring the subject for cardiac side effects and CNS side effects following any inadvertent administration of the pharmaceutical composition into the vasculature of the subject; and C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of treating pain in a subject, the method comprising:

A) administering into the subject in a first time period in proximity to a wound in the subject an amount of a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, B) monitoring the subject for cardiac side effects and CNS side effects following any inadvertent administration of the pharmaceutical composition into the vasculature of the subject; and C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments of the above methods, if it is determined following the step of administering the additional amount of the pharmaceutical composition, that inadvertent administration of the pharmaceutical composition has occurred in that step, the subject may be further monitored for cardiac side effects and CNS side effects. If such cardiac side effects and CNS side effects are absent in the subject, a further additional amount of the pharmaceutical composition may be administered into the subject over a further additional time period, wherein the further additional amount may be the same as or different from the additional amount and the further additional time period may be the same as or different from the additional time period.

Still further additional amounts of the pharmaceutical composition may each be administered in subsequent steps into the subject, while monitoring the subject for cardiac side effects and CNS side effects for any step where inadvertent administration of the pharmaceutical composition is determined to have occurred, until cardiac side effects and/or CNS side effects are present in the subject or until the subject does not feel pain.

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, wherein the pharmaceutical composition comprises: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, the method comprising:
- A) administering into the subject in a first time period in proximity to a wound in the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
- B) determining that inadvertent administration of the pharmaceutical composition into the vasculature of the subject has occurred;
- C) if the inadvertent administration of the pharmaceutical composition in step B) is determined to have occurred, monitoring the subject for cardiac side effects and CNS side effects; and
- D) if cardiac side effects and CNS side effects are absent in the subject, administering into the subject in an additional time period which is the same or different as the first time period in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, wherein the pharmaceutical composition comprises a multivesicular liposome comprising bupivacaine phosphate; a lipid component comprising at least one amphipathic lipid and at least one neutral lipid lacking a hydrophilic head group; and, optionally, a cholesterol and/or a plant sterol, the method comprising:
- A) administering into the subject in a first time period in proximity to a wound in the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
- B) determining that inadvertent administration of the pharmaceutical composition into the vasculature of the subject has occurred;
- C) if the inadvertent administration of the pharmaceutical composition in step B) is determined to have occurred, monitoring the subject for cardiac side effects and CNS side effects; and
- D) if cardiac side effects and CNS side effects are absent in the subject, administering into the subject in an additional time period which is the same or different as the first time period in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, wherein the pharmaceutical composition comprises multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
- a) preparing a first aqueous component comprising phosphoric acid;
- b) preparing a lipid component comprising at least one organic solvent, at least one amphipathic lipid, and at least one neutral lipid lacking a hydrophilic head group;
- c) mixing said first aqueous component and said lipid component to form a water-in-oil emulsion, wherein at least one component comprises bupivacaine or a salt thereof;
- d) mixing said water-in-oil emulsion with a second aqueous component to form solvent spherules; and
- e) removing the organic solvent from the solvent spherules to form multivesicular liposomes encapsulating bupivacaine phosphate, the method comprising:
- A) administering into the subject in a first time period in proximity to a wound in the subject an amount of the pharmaceutical composition,
- B) determining that inadvertent administration of the pharmaceutical composition into the vasculature of the subject has occurred;
- C) if the inadvertent administration of the pharmaceutical composition in step B) is determined to have occurred, monitoring the subject for cardiac side effects and CNS side effects; and
- D) if cardiac side effects and CNS side effects are absent in the subject, administering into the subject in an additional time period which is the same or different as the first time period in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, wherein the pharmaceutical composition comprises: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, the method comprising:
- A) administering into the subject in a first time period in proximity to a wound in the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi;

B) determining that inadvertent administration of the pharmaceutical composition into the vasculature of the subject has occurred;

C) if the inadvertent administration of the pharmaceutical composition in step B) is determined to have occurred, monitoring the subject for cardiac side effects and CNS side effects; and D) if cardiac side effects and CNS side effects are absent in the subject, administering into the subject in an additional time period which is the same or different as the first time period in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, the method comprising:

A) administering into the subject in a first time period in proximity to a wound in the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi;

B) determining that inadvertent administration of the pharmaceutical composition into the vasculature of the subject has occurred;

C) if the inadvertent administration of the pharmaceutical composition in step B) is determined to have occurred, monitoring the subject for cardiac side effects and CNS side effects; and D) if cardiac side effects and CNS side effects are absent in the subject, administering into the subject in an additional time period which is the same or different as the first time period in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, the method comprising:

A) administering into the subject in a first time period in proximity to a wound in the subject an amount of a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
- B) determining that inadvertent administration of the pharmaceutical composition into the vasculature of the subject has occurred;
- C) if the inadvertent administration of the pharmaceutical composition in step B) is determined to have occurred, monitoring the subject for cardiac side effects and CNS side effects; and
- D) if cardiac side effects and CNS side effects are absent in the subject, administering into the subject in an additional time period which is the same or different as the first time period in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject,
the method comprising:
- A) administering into the subject in a first time period in proximity to a wound in the subject an amount of a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
- wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
- B) determining that inadvertent administration of the pharmaceutical composition into the vasculature of the subject has occurred;
- C) if the inadvertent administration of the pharmaceutical composition in step B) is determined to have occurred, monitoring the subject for cardiac side effects and CNS side effects; and
- D) if cardiac side effects and CNS side effects are absent in the subject, administering into the subject in an additional time period which is the same or different as the first time period in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, wherein the pharmaceutical composition comprises: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
the method comprising:
- A) administering into the subject in a first time period in proximity to a wound in the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
- B) monitoring the subject for cardiac side effects and CNS side effects following any inadvertent administration of the pharmaceutical composition into the vasculature of the subject; and
- C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, wherein the pharmaceutical composition comprises a multivesicular liposome comprising bupivacaine phosphate; a lipid component comprising at least one amphipathic lipid and at least one neutral lipid lacking a hydrophilic head group; and, optionally, a cholesterol and/or a plant sterol,
the method comprising:
- A) administering into the subject in a first time period in proximity to a wound in the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
- B) monitoring the subject for cardiac side effects and CNS side effects following any inadvertent administration of the pharmaceutical composition into the vasculature of the subject; and
- C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, wherein the pharmaceutical composition comprises multivesicular liposomes encapsulating bupivacaine phosphate, said multivesicular liposomes comprising
 bupivacaine or a salt thereof;
 phosphoric acid;
 a lipid component comprising at least one amphipathic lipid and at least one neutral lipid lacking a hydrophilic head group; and,
 optionally, a cholesterol and/or a plant sterol wherein said multivesicular liposomes are made by a process comprising:
 a) preparing a first aqueous component comprising phosphoric acid;
 b) preparing a lipid component comprising at least one organic solvent, at least one amphipathic lipid, and at least one neutral lipid lacking a hydrophilic head group;
 c) mixing said first aqueous component and said lipid component to form a water-in-oil emulsion, wherein at least one component comprises bupivacaine or a salt thereof;
 d) mixing said water-in-oil emulsion with a second aqueous component to form solvent spherules; and
 e) removing the organic solvent from the solvent spherules to form multivesicular liposomes encapsulating bupivacaine phosphate,
 the method comprising:
 A) administering into the subject in a first time period in proximity to a wound in the subject an amount of the pharmaceutical composition
 B) monitoring the subject for cardiac side effects and CNS side effects following any inadvertent administration of the pharmaceutical composition into the vasculature of the subject;
 and
 C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject, wherein the pharmaceutical composition comprises: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
 the method comprising:
 A) administering into the subject in a first time period in proximity to a wound in the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
 B) monitoring the subject for cardiac side effects and CNS side effects following any inadvertent administration of the pharmaceutical composition into the vasculature of the subject;
 and
 C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject,
 the method comprising:
 A) administering into the subject in a first time period in proximity to a wound in the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, B) monitoring the subject for cardiac side effects and CNS side effects following any inadvertent administration of the pharmaceutical composition into the vasculature of the subject;
and
C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject,
the method comprising:
A) administering into the subject in a first time period in proximity to a wound in the subject an amount of a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, B) monitoring the subject for cardiac side effects and CNS side effects following any inadvertent administration of the pharmaceutical composition into the vasculature of the subject;
and
C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments provided herein is a method of determining a total amount of a dose of a pharmaceutical composition suitable for treating pain in a subject, wherein the administration is susceptible to concomitant inadvertent administration of the pharmaceutical composition into the vasculature of the subject,
the method comprising:
A) administering into the subject in a first time period in proximity to a wound in the subject an amount of a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, B) monitoring the subject for cardiac side effects and CNS side effects following any inadvertent administration of the pharmaceutical composition into the vasculature of the subject;
and
C) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A).

In some embodiments of the above methods, if it is determined following the step of administering the additional amount of the pharmaceutical composition, that inadvertent administration of the pharmaceutical composition has occurred in that step, the subject may be further monitored for cardiac side effects and CNS side effects. If such cardiac side effects and CNS side effects are absent in the subject, a further additional amount of the pharmaceutical composition may be administered into the subject over a further additional time period, wherein the further additional amount may be the same as or different from the additional amount and the further additional time period may be the same as or different from the additional time period. Still further additional amounts of the pharmaceutical composition may each be administered in subsequent steps into the subject, while monitoring the subject for cardiac side effects and CNS side effects for any step where inadvertent administration of the pharmaceutical composition is determined to have occurred, until cardiac side effects and/or CNS side effects are present in the subject or until the subject does not feel pain.

In such embodiments of a method of determining a total amount of a dose of a pharmaceutical composition suitable for treating pain in the subject, the total amount is equal to the sum of
the amount administered in step A);
the additional amount administered;
if applicable, the further additional amount, and
if applicable, each still further additional amount.
In such embodiments of a method of determining a total amount of a dose of a pharmaceutical composition suitable for treating pain in the subject, the total amount is equal to the sum of
the amount administered in step A);
the additional amount administered;
if applicable, the further additional amount, and
if applicable, each still further additional amount.

In some embodiments provided herein is a method of anesthetizing a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
  wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
  wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of anesthetizing a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of anesthetizing a subject in need thereof, the method comprising administering into the subject in proximity to a wound in the subject a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of anesthetizing a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of anesthetizing a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of anesthetizing a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of anesthetizing a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of anesthetizing a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of anesthetizing a subject in need thereof, the method comprising administering into the subject in proximity to a wound in the subject a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of anesthetizing a subject in need thereof, the method comprising administering into the subject in proximity to a wound in the subject a multivesicular liposomal particle pharmaceutical composition made by a process comprising:
a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of anesthetizing a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of anesthetizing a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing pain in a subject, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing pain in a subject, the method comprising administering into the subject in proximity to a wound in the subject a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject does not result in cardiac side effects or CNS side effects in the subject.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject does not result in cardiac side effects or CNS side effects in the subject.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising multivesicular liposomes encapsulating bupivacaine phosphate, said multivesicular liposomes comprising bupivacaine or a salt thereof;

phosphoric acid;

a lipid component comprising at least one amphipathic lipid and at least one neutral lipid lacking a hydrophilic head group; and, optionally, a cholesterol and/or a plant sterol wherein said multivesicular liposomes are made by a process comprising:

a) preparing a first aqueous component comprising phosphoric acid;

b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, wherein inadvertent administration of the pharmaceutical composition into the vasculature of the subject does not result in cardiac side effects or CNS side effects in the subject.

In some embodiments provided herein is a method of reducing an amount of an analgesic, such as an opioid, or such as a non-opioid analgesic, administered to a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject does not result in cardiac side effects or CNS side effects in the subject.

In some embodiments provided herein is a method of reducing an amount of an analgesic, such as an opioid, or such as a non-opioid analgesic, administered to a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject does not result in cardiac side effects or CNS side effects in the subject.

In some embodiments provided herein is a method of reducing an amount of an analgesic, such as an opioid, or such as a non-opioid analgesic, administered to a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject does not result in cardiac side effects or CNS side effects in the subject.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing an amount of an analgesic, such as an opioid, or such as a non-opioid analgesic, administered to a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing an amount of an analgesic, such as an opioid, or such as a non-opioid analgesic, administered to a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing an amount of an analgesic, such as an opioid, or such as a non-opioid analgesic, administered to a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
 phosphoric acid;
 a lipid component comprising at least one amphipathic lipid and at least one neutral lipid lacking a hydrophilic head group; and,
 optionally, a cholesterol and/or a plant sterol wherein said multivesicular liposomes are made by a process comprising:
 a) preparing a first aqueous component comprising phosphoric acid;
 b) preparing a lipid component comprising at least one organic solvent, at least one amphipathic lipid, and at least one neutral lipid lacking a hydrophilic head group;
 c) mixing said first aqueous component and said lipid component to form a water-in-oil emulsion, wherein at least one component comprises bupivacaine or a salt thereof;
 d) mixing said water-in-oil emulsion with a second aqueous component to form solvent spherules; and
 e) removing the organic solvent from the solvent spherules to form multivesicular liposomes encapsulating bupivacaine phosphate,
 wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing an amount of an analgesic, such as an opioid, or such as a non-opioid analgesic, administered to a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing an amount of an analgesic, such as an opioid, or such as a non-opioid analgesic, administered to a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing an amount of an analgesic, such as an opioid, or such as a non-opioid analgesic, administered to a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method reducing a duration of time during which an analgesic, such as an opioid, or such as a non-opioid analgesic, is administered to a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
  wherein inadvertent administration of the pharmaceutical composition into the vasculature of the subject does not result in cardiac side effects or CNS side effects in the subject.

In some embodiments provided herein is a method reducing a duration of time during which an analgesic, such as an opioid, or such as a non-opioid analgesic, is administered to a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject does not result in cardiac side effects or CNS side effects in the subject.

In some embodiments provided herein is a method reducing a duration of time during which an analgesic, such as an opioid, or such as a non-opioid analgesic, is administered to a subject in need thereof, the method comprising administering into the subject in proximity to a wound in the subject a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  wherein inadvertent administration of the pharmaceutical composition into the vasculature of the subject does not result in cardiac side effects or CNS side effects in the subject.

In some embodiments provided herein is a method reducing a duration of time during which an analgesic, such as an opioid, or such as a non-opioid analgesic, is administered to a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject does not result in cardiac side effects or CNS side effects in the subject.

In some embodiments provided herein is a method reducing a duration of time during which an analgesic, such as an opioid, or such as a non-opioid analgesic, is administered to a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject does not result in cardiac side effects or CNS side effects in the subject.

In some embodiments provided herein is a method reducing a duration of time during which an analgesic, such as an opioid, or such as a non-opioid analgesic, is administered to a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject does not result in cardiac side effects or CNS side effects in the subject.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method reducing a duration of time during which an analgesic, such as an opioid, or such as a non-opioid analgesic, is administered to a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method reducing a duration of time during which an analgesic, such as an opioid, or such as a non-opioid analgesic, is administered to a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
  wherein inadvertent administration of the pharmaceutical composition into the vasculature of the subject provides a plasma Cmax of bupivacaine that is lower than the plasma Cmax of bupivacaine in the subject following administration into the vasculature of the subject of an amount of a non-liposomal bupivacaine, wherein the amount of the pharmaceutical composition and the amount of the non-liposomal bupivacaine are equivalent to the same amount of bupivacaine.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some embodiments provided herein is a method of reducing a duration of time during which an analgesic, such as an opioid, or such as a non-opioid analgesic, is administered to a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject.

In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method of treating pain in a subject, the method comprising:
a) cautiously administering into the subject in a first time period in proximity to a wound in the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
and
b) monitoring the plasma level of bupivacaine in the subject.

In some embodiments provided herein is a method of treating pain in a subject, the method comprising:
a) cautiously administering into the subject in a first time period in proximity to a wound in the subject an amount of a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
and
b) monitoring the plasma level of bupivacaine in the subject.

In some embodiments provided herein is a method of treating pain in a subject, the method comprising:
- A) cautiously administering into the subject in a first time period in proximity to a wound in the subject an amount of a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  - a) preparing a first aqueous component comprising phosphoric acid;
  - b) preparing a lipid component comprising at least one organic solvent, at least one amphipathic lipid, and at least one neutral lipid lacking a hydrophilic head group;
  - c) mixing said first aqueous component and said lipid component to form a water-in-oil emulsion, wherein at least one component comprises bupivacaine or a salt thereof;
  - d) mixing said water-in-oil emulsion with a second aqueous component to form solvent spherules; and
  - e) removing the organic solvent from the solvent spherules to form multivesicular liposomes encapsulating bupivacaine phosphate, and
- B) monitoring the plasma level of bupivacaine in the subject.

In some embodiments provided herein is a method of treating pain in a subject, the method comprising:
- A) cautiously administering into the subject in a first time period in proximity to a wound in the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, and
- B) monitoring the plasma level of bupivacaine in the subject.

In some embodiments provided herein is a method of treating pain in a subject, the method comprising:
- A) cautiously administering into the subject in a first time period in proximity to a wound in the subject an amount of a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, and
- B) monitoring the plasma level of bupivacaine in the subject.

In some embodiments provided herein is a method of treating pain in a subject, the method comprising:
- A) cautiously administering into the subject in a first time period in proximity to a wound in the subject an amount of a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, and B) monitoring the plasma level of bupivacaine in the subject.

In some more particular embodiments, the method further comprises:

C) determining that the plasma level of bupivacaine in the subject at a time point following the administering of the pharmaceutical composition is less than 2,000 ng/mL, such as less than 1,500 ng/mL, such as less than 1,000 ng/mL, such as less than 500 ng/mL; and D) cautiously administering into the subject in an additional time period, which is the same or different as the first time period, in proximity to the wound an additional amount of the pharmaceutical composition to the subject, wherein the additional amount is the same as or greater than the amount in step A).

In some more particular embodiments, the pharmaceutical composition is administered in an amount equivalent to about 10 mg to about 300 mg of bupivacaine. In some more particular embodiments, the pharmaceutical composition is administered in an amount equivalent 133 mg to 266 mg of bupivacaine.

In some embodiments provided herein is a method of treating pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject does not result in cardiac side effects or CNS side effects in the subject.

In some embodiments provided herein is a method of treating pain in a subject, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;

b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, wherein inadvertent administration of the pharmaceutical composition into the vasculature of the subject does not result in cardiac side effects or CNS side effects in the subject.

In some more particular embodiments, the pharmaceutical composition is administered in an amount equivalent to about 10 mg to about 300 mg of bupivacaine. In some more particular embodiments, the pharmaceutical composition is administered in an amount equivalent 133 mg to 266 mg of bupivacaine. In some embodiments provided herein is a method of treating pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject does not result in cardiac side effects or CNS side effects in the subject.

In some embodiments provided herein is a method of treating pain in a subject, the method comprising:

A) cautiously administering into the subject in a first time period in proximity to a wound in the subject an amount of a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, and B) monitoring the plasma level of bupivacaine in the subject.

In some embodiments provided herein is a method of treating pain in a subject, the method comprising:

A) cautiously administering into the subject in a first time period in proximity to a wound in the subject an amount of a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, and B) monitoring the plasma level of bupivacaine in the subject.

In some embodiments provided herein is a method of treating pain in a first subject, the method comprising administering into the first subject in proximity to a wound in the first subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein in a first time period following administration of the pharmaceutical composition into the first subject an analgesic, such as an opioid or such as a non-opioid analgesic, is administered to the first subject in a total amount that is lower than the total amount of the analgesic that is administered to a second subject in a second time period equal to the first time period following administration into the second subject in proximity to a wound in the second subject of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered into the second subject.

In some embodiments provided herein is a method of treating pain in a first subject, the method comprising administering into the first subject in proximity to a wound in the first subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein in a first time period following administration of the pharmaceutical composition into the first subject an analgesic, such as an opioid or such as a non-opioid analgesic, is administered to the first subject in a total amount that is lower than the total amount of the analgesic that is administered to a second subject in a second time period equal to the first time period following administration into the second subject in proximity to a wound in the second subject of non-liposomal bupivacaine containing the same amount of bupivacaine as the pharmaceutical composition, wherein the pharmaceutical composition is not administered into the second subject.

In some embodiments provided herein is a method of treating pain in a first subject, the method comprising administering into the first subject in proximity to a wound in the first subject a pharmaceutical composition comprising: a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, wherein in a first time period following administration of the pharmaceutical composition into the first subject an analgesic, such as an opioid or such as a non-opioid analgesic, is administered to the first subject in a total amount that is lower than the total amount of the analgesic that is administered to a second subject in a second time period equal to the first time period following administration into the second subject in proximity to a wound in the second subject of non-liposomal bupivacaine containing the same amount of bupivacaine as the pharmaceutical composition, wherein the pharmaceutical composition is not administered into the second subject.

In some embodiments provided herein is a method of treating pain in a first subject, the method comprising administering into the first subject in proximity to a wound in the first subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein in a first time period following administration of the pharmaceutical composition into the first subject an analgesic, such as an opioid or such as a non-opioid analgesic, is administered to the first subject in a total amount that is lower than the total amount of the analgesic that is administered to a second subject in a second time period equal to the first time period following administration into the second subject in proximity to a wound in the second subject of non-liposomal bupivacaine containing the same amount of bupivacaine as the pharmaceutical composition, wherein the pharmaceutical composition is not administered into the second subject.

In some embodiments provided herein is a method of treating pain in a first subject, the method comprising administering into the first subject in proximity to a wound in the first subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein in a first time period following administration of the pharmaceutical composition into the first subject an analgesic, such as an opioid or such as a non-opioid analgesic, is administered to the first subject in a total amount that is lower than the total amount of the analgesic that is administered to a second subject in a second time period equal to the first time period following administration into the second subject in proximity to a wound in the second subject of non-liposomal bupivacaine containing the same amount of bupivacaine as the pharmaceutical composition, wherein the pharmaceutical composition is not administered into the second subject.

In some embodiments provided herein is a method of treating pain in a first subject, the method comprising administering into the first subject in proximity to a wound in the first subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein in a first time period following administration of the pharmaceutical composition into the first subject an analgesic, such as an opioid or such as a non-opioid analgesic, is administered to the first subject in a total amount that is lower than the total amount of the analgesic that is administered to a second subject in a second time period equal to the first time period following administration into the second subject in proximity to a wound in the second subject of non-liposomal bupivacaine containing the same amount of bupivacaine as the pharmaceutical composition, wherein the pharmaceutical composition is not administered into the second subject.

In some embodiments, each of the first time period or the second time period may be a time period between 12 hours and 72 hours, such as from about 12 hours to about 24 hours, such as from about 24 hours to about 36 hours, such as from about 36 hours to about 48 hours, such as from about 48 hours to about to about 60 hours, such as from about 60 hours to about 72 hours.

In some embodiments provided herein is a method of anesthetizing a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject does not result in cardiac side effects or CNS side effects in the subject.

In some embodiments provided herein is a method of anesthetizing a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject does not result in cardiac side effects or CNS side effects in the subject.

In some embodiments provided herein is a method of reducing pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject does not result in cardiac side effects or CNS side effects in the subject.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol, wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject.

In some embodiments provided herein is a method of reducing an amount of an analgesic, such as an opioid, or such as a non-opioid analgesic, administered to a subject in need thereof, the method comprising administering into the subject in proximity to a wound in the subject a pharmaceutical composition comprising multivesicular liposomes encapsulating bupivacaine phosphate, said multivesicular liposomes comprising bupivacaine or a salt thereof;
    phosphoric acid;
    a lipid component comprising at least one amphipathic lipid and at least one neutral lipid lacking a hydrophilic head group; and,
    optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject.

In some embodiments provided herein is a method of reducing an amount of an analgesic, such as an opioid, or such as a non-opioid analgesic, administered to a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method of reducing pain in a subject, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method of reducing pain in a subject, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments cardiac side effects are associated with and/or correlated to plasma levels of bupivacaine, such as the plasma Cmax of bupivacaine, in the subject. Examples of such cardiac side effects include: depression of cardiac conductivity, atrioventricular block, ventricular arrhythmias, cardiac arrest, depression of myocardial contractility, peripheral vasodilation, decrease in cardiac output and in arterial blood pressure, tachycardia, sinus tachycardia, ventricular tachycardia, and bradycardia.

In some embodiments CNS side effects are side effects associated with and/or correlated to plasma levels of bupivacaine, such as the plasma Cmax of bupivacaine, in the subject. CNS side effects may be one or more of the following: nausea, vomiting, chills, constriction of the pupils, tinnitus, numbness of tongue, nervousness, dizziness, blurred vision, tremors, drowsiness, convulsions, unconsciousness, seizures, and respiratory arrest. Drowsiness may merge into unconsciousness and respiratory arrest. Cardiac side effects may be one or more of the following: depression of the myocardium, blood pressure changes (usually hypotension), and cardiac arrest.

In some embodiments provided herein is a method reducing a duration of time during which an analgesic, such as an opioid, or such as a non-opioid analgesic, is administered to a subject in need thereof, the method comprising administering into the subject in proximity to a wound in the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method reducing a duration of time during which an analgesic, such as an opioid, or such as a non-opioid analgesic, is administered to a subject in need thereof, the method comprising administering into the subject in proximity to a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method reducing a duration of time during which an analgesic, such as an opioid, or such as a non-opioid analgesic, is administered to a subject in need thereof, the method comprising administering into the subject in proximity to a wound in the subject a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method reducing a duration of time during which an analgesic, such as an opioid, or such as a non-opioid analgesic, is administered to a subject in need thereof, the method comprising administering into the subject in proximity to a wound in the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method reducing a duration of time during which an analgesic, such as an opioid, or such as a non-opioid analgesic, is administered to a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns,
wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method reducing a duration of time during which an analgesic, such as an opioid, or such as a non-opioid analgesic, is administered to a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments the at least one polyhydroxy carboxylic acid is selected from the group consisting of glucuronic acid, gluconic acid and tartaric acid.

In some embodiments the amphipathic lipid is selected from the group consisting of phosphatidylcholines, phosphatidylethanolamines, sphingomyelins, lysophosphatidylcholines, lysophosphatidylethanolamines, phosphatidylglycerols, phosphatidylserines, phosphatidylinositols, phosphatidic acids, cardiolipins, diacyl dimethylammonium propanes, and stearylamines.

In some embodiments the neutral lipid comprises at least one triglyceride.

In some embodiments the method comprises administering a therapeutically effective amount of the pharmaceutical composition.

In some embodiments the pharmaceutical composition comprises a therapeutically effective amount of bupivacaine phosphate. In some embodiments wherein the pharmaceutical composition comprises an amount equivalent to from about 10 mg to about 300 mg of bupivacaine. In some embodiments the pharmaceutical composition comprises an amount equivalent to from about 133 mg to about 266 mg of bupivacaine. In some embodiments the pharmaceutical composition comprises an amount equivalent to from about 10 mg to about 70 mg of bupivacaine. In some embodiments the pharmaceutical composition comprises an amount equivalent to from about 20 mg to about 60 mg of bupivacaine. In some embodiments the pharmaceutical composition comprises an amount equivalent to from about 20 mg to about 50 mg of bupivacaine. In some embodiments the pharmaceutical composition comprises an amount equivalent to from about 20 mg to about 40 mg of bupivacaine. In some embodiments the pharmaceutical composition comprises an amount equivalent to from about 20 mg to about 30 mg of bupivacaine. In some embodiments the pharmaceutical composition comprises an amount equivalent to from about 30 mg to about 60 mg of bupivacaine. In some embodiments the pharmaceutical composition comprises an amount equivalent to from about 30 mg to about 50 mg of bupivacaine. In some embodiments the pharmaceutical composition comprises an amount equivalent to from about 30 mg to about 40 mg of bupivacaine. In some embodiments the amount of the pharmaceutical composition described herein is equivalent to from about 10 mg to about 70 mg of bupivacaine. In some embodiments the amount of the pharmaceutical composition described herein is equivalent to from about 10 mg to about 60 mg of bupivacaine. In some embodiments the amount of the pharmaceutical composition described herein is equivalent to from about 20 mg to about 60 mg of bupivacaine. In some embodiments the amount of the pharmaceutical composition described herein is equivalent to from about 20 mg to about 50 mg of bupivacaine. In some embodiments the amount of the pharmaceutical composition described herein is equivalent to from about 20 mg to about 40 mg of bupivacaine. In some embodiments the amount of the pharmaceutical composition described herein is equivalent to from about 20 mg to about 30 mg of bupivacaine. In some embodiments the amount of the pharmaceutical composition described herein is equivalent to from about 30 mg to about 60 mg of bupivacaine. In some embodiments the amount of the pharmaceutical composition described herein is equivalent to from about 30 mg to about 50 mg of bupivacaine. In some embodiments the amount of the pharmaceutical composition described herein is equivalent to from about 30 mg to about 40 mg of bupivacaine.

In some embodiments, the pain that may be treated according to the methods disclosed herein is pain associated with a wound.

In some embodiments, the pain that may be treated according to the methods disclosed herein is pain associated with a wound.

In some embodiments the method comprises administering an analgesic, such as an opioid, to the subject following the administration of the pharmaceutical composition into the subject.

In some embodiments of the methods herein, the opioid is administered in a total amount less than 200 mg, such as less than 100 mg, such as less than 50 mg, such as less than 25 mg, such as less than 15 mg, in the first about 72 hours following the administration of the pharmaceutical composition into the subject. In some embodiments, the opioid is oxycodone and the method comprises administering oxycodone in a total amount less than or equal to 10 mg or administering morphine in a total amount less than or equal to 15 mg. in the first about 72 hours following the administration of the pharmaceutical composition into the subject. In some embodiments, the method comprises administering one or more morphinans to the subject. In some embodiments, the method comprises administering morphine to the subject. In some more particular embodiments, the morphine is administered to the subject for up to 72 hours following the administration of the pharmaceutical composition into the subject.

In some embodiments, the method comprises administering one or more analgesics to the subject, such as one or more non-opioid analgesics, such as one or more NSAIDs to the subject, following the administration of the pharmaceutical composition into the subject. In some embodiments, the method comprises administering one or more of ketorolac, acetaminophen or ibuprofen to the subject. In some embodiments, the method comprises administering two or more of ketorolac, acetaminophen or ibuprofen to the subject. In some embodiments, the method comprises administering ketorolac, acetaminophen and ibuprofen to the subject. In some more particular embodiments, the analgesic, such as the NSAID, such as the one or more of ketorolac, acetaminophen or ibuprofen, is administered to the subject for up to 72 hours following the administration of the pharmaceutical composition into the subject.

In some embodiments of the methods herein, the method comprises administering into the subject the pharmaceutical composition at a distance of less than about 20 cm, such as less than about 10 cm, from the wound.

In some embodiments of the methods herein, the method comprises administering into the subject the pharmaceutical composition at a distance of less than about 5 cm, such as less than about 2 cm, such as less than about 1 cm, such as less than about 0.5 cm, such as less than about 0.1 cm, from the wound.

In some embodiments, the subject has an AUC for VAS pain intensity scores over the first 72 hours following the administration of the pharmaceutical composition into the subject of from about 100 to about 200, such as about 125 to 175.

In some embodiments of the methods herein, the subject has a distress from itchiness score as determined by the OBAS scale of less than 4, such as 0, 1, 2 or 3, following the administration of the pharmaceutical composition into the subject.

As used herein, a "wound" may be an internal wound or an external wound that has not formed a scar. In some embodiments, the wound is actively bleeding.

In some embodiments of the methods herein, the plasma Cmax of bupivacaine in the subject is about 150 ng/mL to about 250 ng/mL, such as about 175 ng/mL to about 225 ng/mL, such as about 200 ng/mL, such as about 210 mg/mL, for an amount of the pharmaceutical composition described herein that is equivalent to about 133 mg of bupivacaine. In some embodiments, the Cmax occurs after about 48 hours following administration of the pharmaceutical composition. In some embodiments, the Cmax occurs after about 72 hours following administration of the pharmaceutical composition.

In some embodiments of the methods herein, the plasma Cmax of bupivacaine in the subject is about 300 ng/mL to about 550 ng/mL, such as about 350 ng/mL to about 500 ng/mL, such as about 450 mg/mL, such as about 460 ng/mL, for an amount of the pharmaceutical composition described herein that is equivalent to about 266 mg of bupivacaine. In some embodiments, the Cmax occurs after about 48 hours following administration of the pharmaceutical composition. In some embodiments, the Cmax occurs after about 72 hours following administration of the pharmaceutical composition.

In some embodiments of the methods herein, the plasma Cmax of bupivacaine in the subject is less than about 850 ng/mL, such as less than about 800 ng/mL, such as less than about 750 ng/mL, such as less than about 700 ng/mL, such as less than about 650 ng/mL, such as less than about 600 ng/mL.

In some embodiments of the method of treating pain in a subject, comprising
  a) administering into the subject in a first time period in proximity to a wound in the subject an amount of a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome,
  b) determining that inadvertent administration of the pharmaceutical composition into the vasculature of the subject has occurred;
  c) if the inadvertent administration of the pharmaceutical composition in step b) is determined to have occurred, monitoring the subject for cardiac side effects and CNS side effects;

and
d) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step a), the amount in step a) is an amount equivalent to about 133 mg of bupivacaine to about 266 mg of bupivacaine. In some more particular embodiments, the additional amount is an amount equivalent to about 133 mg of bupivacaine.

In some embodiments of the method of treating pain in a subject, comprising
  a) administering into the subject in a first time period in proximity to a wound in the subject an amount of a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
  b) determining that inadvertent administration of the pharmaceutical composition into the vasculature of the subject has occurred;
  c) if the inadvertent administration of the pharmaceutical composition in step b) is determined to have occurred, monitoring the subject for cardiac side effects and CNS side effects; and
  d) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step a), the amount in step a) is an amount equivalent to about 133 mg of bupivacaine to about 266 mg of bupivacaine. In some more particular embodiments, the additional amount is an amount equivalent to about 133 mg of bupivacaine.

In some embodiments of the method of treating pain in a subject, comprising
  A) administering into the subject in a first time period in proximity to a wound in the subject an amount of a pharmaceutical composition comprising multivesicular liposomes encapsulating bupivacaine phosphate, said multivesicular liposomes comprising
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate,
  B) determining that inadvertent administration of the pharmaceutical composition into the vasculature of the subject has occurred;
  C) if the inadvertent administration of the pharmaceutical composition in step B) is determined to have occurred, monitoring the subject for cardiac side effects and CNS side effects;
  and
  D) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A), the amount in step A) is an amount equivalent to about 133 mg of bupivacaine to about 266 mg of bupivacaine. In some more particular embodiments, the additional amount is an amount equivalent to about 133 mg of bupivacaine.

In some embodiments of the method of treating pain in a subject, comprising
  A) administering into the subject in a first time period in proximity to a wound in the subject an amount of a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
  B) determining that inadvertent administration of the pharmaceutical composition into the vasculature of the subject has occurred;
  C) if the inadvertent administration of the pharmaceutical composition in step B) is determined to have occurred, monitoring the subject for cardiac side effects and CNS side effects;

and

D) if cardiac side effects and CNS side effects are absent in the subject, administering into the subject in an additional time period, which is the same or different as the first time period, in proximity to the wound an additional amount of the pharmaceutical composition to the subject, wherein the additional amount is the same as or greater than the amount in step A), the amount in step A) is an amount equivalent to about 133 mg of bupivacaine to about 266 mg of bupivacaine. In some more particular embodiments, the additional amount is an amount equivalent to about 133 mg of bupivacaine.

In some embodiments provided herein is a method reducing a duration of time during which an analgesic, such as an opioid, or such as a non-opioid analgesic, is administered to a subject in need thereof, the method comprising administering into the subject in proximity to a wound in the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method reducing a duration of time during which an analgesic, such as an opioid, or such as a non-opioid analgesic, is administered to a subject in need thereof, the method comprising administering into the subject in proximity to a wound in the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, wherein inadvertent administration of the pharmaceutical composition into the vasculature of the subject does not result in cardiac side effects or CNS side effects in the subject. In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments, the subject is a human.

In some embodiments, the subject is a non-human animal.

In some embodiments, the subject is a dog.

In some embodiments, the first subject is a human.

In some embodiments, the first subject is a non-human animal.

In some embodiments, the first subject is a dog.

In some embodiments, the method does not comprise administering an analgesic, such as an opioid, to the subject following the administration of the pharmaceutical composition into the subject.

In some embodiments, the method does not comprise administering one or more morphinans to the subject following the administration of the pharmaceutical composition into the subject. In some embodiments, the method does not comprise administering morphine to the subject following the administration of the pharmaceutical composition into the subject.

In some embodiments, the method does not comprise administering an opioid to the first subject following the administration of the pharmaceutical composition into the subject.

In some embodiments, the method comprises administering into the subject an amount of the pharmaceutical composition described herein that is equivalent to about 10 to about 300 mg of bupivacaine. In some embodiments, the method comprises administering into the subject an amount of the pharmaceutical composition described herein that is equivalent to about 100 to about 300 mg of bupivacaine. In some embodiments the amount of the pharmaceutical composition described herein is equivalent to from about 10 mg to about 70 mg of bupivacaine. In some embodiments the amount of the pharmaceutical composition described herein is equivalent to from about 10 mg to about 60 mg of bupivacaine. In some embodiments the amount of the pharmaceutical composition described herein is equivalent to from about 20 mg to about 60 mg of bupivacaine. In some embodiments the amount of the pharmaceutical composition described herein is equivalent to from about 20 mg to about 50 mg of bupivacaine. In some embodiments the amount of the pharmaceutical composition described herein is equivalent to from about 20 mg to about 40 mg of bupivacaine. In some embodiments the amount of the pharmaceutical composition described herein is equivalent to from about 20 mg to about 30 mg of bupivacaine. In some embodiments the amount of the pharmaceutical composition described herein is equivalent to from about 30 mg to about 60 mg of bupivacaine. In some embodiments the amount of the pharmaceutical composition described herein is equivalent to from about 30 mg to about 50 mg of bupivacaine. In some embodiments the amount of the pharmaceutical composition described herein is equivalent to from about 30 mg to about 40 mg of bupivacaine. In some embodiments the amount of the pharmaceutical composition described herein is equivalent to 13.3 mg of bupivacaine. In some embodiments the amount of the pharmaceutical composition described herein is equivalent to 26.6 mg of bupivacaine. In some embodiments the amount of the pharmaceutical composition described herein is equivalent to 39.9 mg of bupivacaine. In some embodiments the amount of the pharmaceutical composition described herein is equivalent to 52.2 mg of bupivacaine. In some embodiments the amount of the pharmaceutical composition described herein is equivalent to 133 mg of bupivacaine. In some embodiments the amount of the pharmaceutical composition described herein is equivalent to 266 mg of bupivacaine.

In some embodiments, the plasma level of bupivacaine in the subject at a time point following the administering of the pharmaceutical composition is from about 2 times to about 4 times less than the plasma level of bupivacaine in the subject at the same time point following administration to the subject of the non-liposomal bupivacaine.

In some embodiments, the plasma level of bupivacaine in the subject following the administering of the pharmaceutical composition is from about 2 times to about 4 times less than the plasma level of bupivacaine in the subject at the same time point that would result from administration to the subject of the non-liposomal bupivacaine.

In some embodiments, the plasma level of bupivacaine in the subject at a time point following the administering of the pharmaceutical composition is at least 2 times less than the plasma level of bupivacaine in the subject at the same time point following administration to the subject of the non-liposomal bupivacaine.

In some embodiments, the plasma level of bupivacaine in the subject following the administering of the pharmaceutical composition is at least 2 times less than the plasma level of bupivacaine in the subject at the same time point that would result from administration to the subject of the non-liposomal bupivacaine.

In some embodiments, the plasma level of bupivacaine in the subject at a time point following the administering of the pharmaceutical composition is at least 3 times less than the plasma level of bupivacaine in the subject at the same time point following administration to the subject of the non-liposomal bupivacaine.

In some embodiments, the plasma level of bupivacaine in the subject following the administering of the pharmaceutical composition is at least 3 times less than the plasma level of bupivacaine in the subject at the same time point that would result from administration to the subject of the non-liposomal bupivacaine.

In some embodiments, the plasma level of bupivacaine in the subject at a time point following the administering of the pharmaceutical composition is about 4 times less than the plasma level of bupivacaine in the subject at the same time point following administration to the subject of the non-liposomal bupivacaine.

In some embodiments, the plasma level of bupivacaine in the subject following the administering of the pharmaceutical composition is about 4 times less than the plasma level of bupivacaine in the subject at the same time point that would result from administration to the subject of the non-liposomal bupivacaine.

In some embodiments, the plasma Cmax of bupivacaine in the subject following the administering of the pharmaceutical composition is from about 2 times to about 4 times less than the plasma Cmax of bupivacaine in the subject following administration to the subject of the non-liposomal bupivacaine.

In some embodiments, the plasma Cmax of bupivacaine in the subject following the administering of the pharmaceutical composition is from about 2 times to about 4 times less than the plasma Cmax of bupivacaine in the subject that would result from administration to the subject of the non-liposomal bupivacaine.

In some embodiments, the plasma Cmax of bupivacaine in the subject following the administering of the pharmaceutical composition is at least 2 times less than the plasma Cmax of bupivacaine in the subject following administration to the subject of the non-liposomal bupivacaine.

In some embodiments, the plasma Cmax of bupivacaine in the subject following the administering of the pharmaceutical composition is at least 2 times less than the plasma Cmax of bupivacaine in the subject that would result from administration to the subject of the non-liposomal bupivacaine.

In some embodiments, the plasma Cmax of bupivacaine in the subject following the administering of the pharmaceutical composition is at least 3 times less than the plasma Cmax of bupivacaine in the subject following administration to the subject of the non-liposomal bupivacaine.

In some embodiments, the plasma Cmax of bupivacaine in the subject following the administering of the pharmaceutical composition is at least 3 times less than the plasma Cmax of bupivacaine in the subject that would result from administration to the subject of the non-liposomal bupivacaine.

In some embodiments, the plasma Cmax of bupivacaine in the subject following the administering of the pharmaceutical composition is about 4 times less than the plasma Cmax of bupivacaine in the subject following administration to the subject of the non-liposomal bupivacaine.

In some embodiments, the plasma Cmax of bupivacaine in the subject following the administering of the pharmaceutical composition is about 4 times less than the plasma Cmax of bupivacaine in the subject that would result from administration to the subject of the non-liposomal bupivacaine.

In some embodiments, the method comprises administering one or more non-opioid analgesics to the subject. In some embodiments, the one or more non-opioid analgesics are one or more NSAIDs. In some embodiments, the one or more non-opioid analgesics are one or more of ketorolac, acetaminophen or ibuprofen. Thus, in some embodiments, the method comprises administering one or more of ketorolac, acetaminophen or ibuprofen to the subject, wherein the one or more of ketorolac, acetaminophen or ibuprofen, is administered to the subject for up to 72 hours following the administration of the pharmaceutical composition into the subject in the following amounts:

IV ketorolac 15 mg once at the time of skin incision closure and prior to the TAP infiltration Intravenous (IV) acetaminophen 1000 mcg at the time of skin incision closure Scheduled oral (PO) acetaminophen 650 mg at the end of surgery and every 6 hours (q6h) for up to 72 hours Scheduled PO ibuprofen 600 mg at the end of surgery and q6h for up to 72 hours In some embodiments, the method comprises administering an opioid to a subject following the administration of the pharmaceutical composition into the subject, wherein one or more opioids are administered in the following amounts:

Oral immediate-release oxycodone at 5-10 mg every 4 hours or as needed

IV morphine at 1-2 mg or hydromorphone initiated at 0.3-0.5 mg every 4 hours or as needed In some embodiments of any of the methods disclosed herein, the method produces postsurgical local analgesia.

In some embodiments of any of the methods disclosed herein, the method produces postsurgical regional analgesia.

In some embodiments of any of the methods disclosed herein, the subject does not experience CNS side effects.

In some embodiments of any of the methods disclosed herein, the subject does not experience cardiac side effects.

Unless otherwise defined, all technical and scientific terms used herein have the same meaning as commonly understood by one of ordinary skill in the art to which this invention belongs. Although methods and materials similar to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Definitions

The term "therapeutically effective" as it pertains to bupivacaine or a salt thereof, such as bupivacaine phosphate, present in the pharmaceutical compositions described herein, means that an anesthetic present in the first aqueous phase within the multivesicular liposome is released in a manner sufficient to achieve a particular level of anesthesia. Exact dosages will vary depending on such factors as the particular anesthetic, as well as patient factors such as age, sex, general condition, and the like. Those of skill in the art can readily take these factors into account and use them to establish effective therapeutic concentrations without resort to undue experimentation.

The term "administering" refers to administering a drug by injection. In some embodiments, in connection with administering the pharmaceutical composition disclosed herein, the method does not comprise administering the composition by intravenous injection. In some embodiments, the method comprises administering the composition by infiltration. In some embodiments, the method comprises administering the composition by interscalene brachial plexus nerve block. In some embodiments, the method comprises administering the composition by transversus abdominis plane (TAP) block. In some embodiments, the method comprises administering the composition by subarachnoid injection.

The term "cautiously administering", when used in connection with administering a pharmaceutical composition as disclosed herein, refers to administering into a subject the pharmaceutical composition in an amount equivalent to less than or equal to about 665 mg of bupivacaine, such as an amount equivalent to less than or equal to about 465 mg of bupivacaine, such as an amount equivalent to less than or equal to about 266 mg of bupivacaine, such as in an amount equivalent to less than or equal to 133 mg of bupivacaine.

As used herein, a "wound" may be an internal wound or an external wound that has not formed a scar. In some embodiments, the wound is actively bleeding.

As used herein, a "VAS pain intensity score" refers to the Visual Analog Scale pain intensity score described in Delgado et al., *J Am Acad Orthop Surg Glob Res Rev.* 2018 March; 2(3): e088 published online 2018 Mar. 23. doi: 10.5435/JAAOSGlobal-D-17-00088, incorporated by reference herein in its entirety.

As used herein, "non-liposomal bupivacaine" refers to bupivacaine that is not in liposomal form. For example, "non-liposomal bupivacaine" refers to bupivacaine that is not comprised in a multivesicular liposome. The terms "non-liposomal bupivacaine" and "free bupivacaine" are used interchangeably herein, and encompass compositions containing bupivacaine, or a salt thereof, that is not in liposomal form.

In some embodiments the compositions used in the methods disclosed herein comprise a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments the aqueous phase further comprises hydrochloric acid.

Multivesicular liposomes or "MVL", which is used herein to refer to a multivesicular liposome or a plurality of multivesicular liposomes, are lipid vesicles having multiple non-concentric internal aqueous chambers having internal membranes distributed as a network throughout the MVL. The chambers may contain acids which are effective to enable the encapsulation of bupivacaine or a salt thereof and to modulate its release rate. A preparation of MVL is described, for example, in Kim et al., Biochim. Biophys. Acta 728, 339-348, 1983. In some embodiments, a MVL is prepared in accordance with a process as described in U.S. Pat. No. 9,192,575, incorporated by reference herein in its entirety. In some embodiments, a MVL is prepared in accordance with a process as described in U.S. Pat. No. 8,182,835, incorporated by reference herein in its entirety. In some embodiments, a MVL is prepared in accordance with a process as described in U.S. Pat. No. 8,834,921, incorporated by reference herein in its entirety. In some embodiments, a MVL is prepared in accordance with a process as described in U.S. Pat. No. 9,205,052, incorporated by reference herein in its entirety.

In some embodiments the multivesicular liposomes ("MVL") are made by the following process. A "water-in-oil" type emulsion containing a non-hydrohalic acid salt of bupivacaine, such as bupivacaine phosphate, is formed from two immiscible phases, a lipid phase and a first aqueous phase. The lipid phase is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholines, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, and stearylamines.

Suitable neutral lipids are triglycerides, propylene glycol esters, ethylene glycol esters, and squalene. Examples of triglycerides useful in the present invention are triolein, tripalmitolein, trimyristolein, trilinolein, tributyrin, tricaproin, tricaprylin, and tricaprin. The fatty chains in the triglycerides useful in the present invention can be all the same, or not all the same (mixed chain triglycerides), including all different. Both saturated and unsaturated fatty chains are useful in the present invention. The propylene glycol esters can be mixed diesters of caprylic and capric acids.

Many types of volatile organic solvents can be used in the present invention, including ethers, esters, halogenated ethers, hydrocarbons, halohydrocarbons, or Freons. For example, diethyl ether, chloroform, tetrahydrofuran, ethyl acetate, Forane, and any combinations thereof are suitable for use in making the compositions of the present invention.

Optionally, other components are included in the lipid phase. Among these are cholesterol or plant sterols.

The first aqueous phase includes bupivacaine or a salt thereof, such as bupivacaine phosphate, at least one polyhydroxy carboxylic acid, and at least one di- or tri-protic mineral acid. In some embodiments, also included is hydrochloric acid. The di- or tri-protic mineral acids include sulfuric acid, and phosphoric acid. Also included in the first aqueous phase are such polyhydroxy carboxylic acids as glucuronic acid, gluconic acid, and tartaric acid. The di- and tri-protic mineral acids and the polyhydroxy organic acids are present in the first aqueous phase in concentrations of from 0.01 mM to about 0.5 M, or preferably from about 5 mM to about 300 mM. When hydrochloric acid is used, it is present in lower amounts, from about 0.1 mM to about 50 mM, or preferably from about 0.5 mM to about 25 mM.

The lipid phase and first aqueous phase are mixed by mechanical turbulence, such as through use of rotating or vibrating blades, shaking, extrusion through baffled structures or porous pipes, by ultrasound, or by nozzle atomization, to produce a water-in-oil emulsion. Thus, bupivacaine or a salt thereof, such as bupivacaine phosphate, is encapsulated directly in the first step of MVL manufacture.

The whole water-in-oil emulsion is then dispersed into a second aqueous phase by means described above, to form solvent spherules suspended in the second aqueous phase. The term "solvent spherules" refers to a microscopic spheroid droplet of organic solvent, within which are suspended multiple smaller droplets of aqueous solution. The resulting solvent spherules therefore contain multiple aqueous droplets with the bupivacaine or a salt thereof, such as bupivacaine phosphate, dissolved therein. The second aqueous phase can contain additional components such as glucose, and/or lysine.

The volatile organic solvent is then removed from the spherules, for instance by surface evaporation from the suspension: When the solvent is substantially or completely evaporated, MVL are formed. Gases which can be used for the evaporation include nitrogen, argon, helium, oxygen, hydrogen, and carbon dioxide. Alternatively, the volatile solvent can be removed by sparging, rotary evaporation, or with the use of solvent selective membranes.

In some embodiments, an MVL is prepared in accordance with a process as described in U.S. Pat. No. 10,398,648, incorporated by reference herein in its entirety. In some embodiments, a MVL is prepared in accordance with a process as described in U.S. Pat. No. 9,585,838 incorporated by reference herein in its entirety.

In some embodiments, a MVL is prepared in accordance with a process as described in US 2011-0250264, US 2013-0306759, US 2013-0177634, US 2013-0177633, US 2013-0177635, US 2013-0195965, US 2013-0177636, US 2013-0183373, US 2013-0177638, US 2013-0177637, US 2013-0183372, US 2013-0183375, US 2016-0361260 or US 2018-0092847, each of which is incorporated by reference herein in its entirety.

EXAMPLES

Example 1

Clinical Trial Outline
Objective
To evaluate the safety and tolerability of EXPAREL® compared to standard bupivacaine when administered via intravenous infusion. EXPAREL® is the trade name for the pharmaceutical composition disclosed herein.

BACKGROUND

Inadvertent intravascular injections of local anesthetics occur frequently in clinical practice. As such, if an encapsulated local anesthetic such as EXPAREL® could demonstrate greater safety and tolerability than standard of care bupivacaine in the case of intravascular injection, such as in the case of intravenous injection, such as in the case of inadvertent intravenous injection, it would be of high value to clinicians.

The current study will first replicate and validate the methods in Scott et al. ((1989), Anesthesia and Analgesia, 1 Nov. 1989, 69(5):563-569, PMID: 2679230) methods using bupivacaine to determine a maximum tolerated dose (MTD, defined as the highest dose at which <50% of subjects report symptoms of early CNS toxicity as determined by the investigator) for bupivacaine administered at 10 mg/minute (Part 1). Scott's methods will then be applied to escalating doses of EXPAREL® until the MTD of EXPAREL® at 10 mg/minute is determined (Part 2A). If the MTD for EXPAREL® is determined to be the highest dose tested, this dose will be administered at increasing rates of speed until the fastest tolerated rate for this dose is found (Part 2B). Data from Parts 1 and 2A/2B will be analyzed to determine the optimum comparison of interest for a randomized, double-blind comparison of EXPAREL® vs. bupivacaine (Part 3).
Familiarization of Subjects with Early CNS Toxicity Symptoms Using Lidocaine
All subjects in all cohorts will receive an IV infusion of lidocaine 7 days prior to their study infusion. Subjects will be educated as to early CNS toxicity symptoms including lightheadedness, tinnitus and numbness of tongue. Lidocaine will be administered at a rate of 100 mg/minute until the subject reports onset of one or more of these symptoms (up to a maximum of 200 mg). The purpose of this technique is to familiarize subjects with the experience of mild early CNS toxicity symptoms, so that they may report them accurately after their study infusion.

Pharmacokinetics and Safety Monitoring

For all subjects in all cohorts, pharmacokinetic blood draws will be gathered from the arm* contralateral to the study drug infusion at appropriate intervals. All subjects will remain in-house for 2-3 days post infusion for safety monitoring and data collection. All subjects will be continually monitored via ECG before, during and after each infusion. An arterial line and two venous catheters will be maintained during and after infusion. All patients will be monitored by continuous pulse oximetry. This will be a hospital-based study; trained personnel equipped with appropriate resuscitative equipment and Intralipid will be nearby/on call for the duration of the inpatient period.

Study Part 1: Bupivacaine 150 mg/Replicate/Validate Scott Techniques

Part 1 will consist of one cohort of 12 patients. Each patient will receive IV infusion of bupivacaine at a rate of 10 mg/minute until one of the following occurs:

Subject reports one or more early CNS toxicity symptoms
150 mg of bupivacaine is administered (15 minutes)

The highest dose of bupivacaine tolerated by 6 of these 12 patients will be considered the bupivacaine MTD.

Study Part 2A: EXPAREL® Dose Escalation/Dose Selection

Part 2A will consist of up to 9 cohorts of 12 patients each. Each patient will receive IV infusion of EXPAREL® at a rate of 10 mg/minute until one of the following occurs:

Subject reports one or more early CNS toxicity symptoms
The full allotted dose of EXPAREL® is administered The maximum dose for each cohort will be as follows:
Cohort 2A-1 150 mg
Cohort 2A-2 165 mg
Cohort 2A-3 180 mg
Cohort 2A-4 195 mg
Cohort 2A-5 210 mg
Cohort 2A-6 225 mg
Cohort 2A-7 240 mg
Cohort 2A-8 255 mg
Cohort 2A-9 266 mg (the dose contained in a full standard vial of EXPAREL®)

If 6/12 patients in any cohort report one or more early CNS toxicity symptoms, Part 2A will be stopped, the dose for the previous cohort will be considered the MTD, and Part 2B below will be skipped (the study will proceed directly to Part 3 with the EXPAREL® MTD administered at 10 mg/minute). If <6/12 patients in all cohorts report any symptom, the study will continue to Part 2B (see below).

After each cohort, data will be reviewed by a safety review committee (SRC) who will determine whether to escalate to the next cohort.

Study Part 2B: Administration Rate Escalation/Selection for Selected EXPAREL® Dose Part 2B will be performed only if Part 2A demonstrates that the highest dose (266 mg) is tolerated, and will consist of up to 11 cohorts of 12 patients each. Each patient will receive IV infusion of 266 mg of EXPAREL® at the rate mandated for their cohort assignment below until one of the following occurs:

Subject reports one or more early CNS toxicity symptoms
The full allotted dose of EXPAREL® is administered The rate for each cohort will be as follows:
Cohort 2B-1 12.5 mg/minute
Cohort 2B-2 15 mg/minute
Cohort 2B-3 20 mg/minute
Cohort 2B-4 30 mg/minute
Cohort 2B-5 40 mg/minute
Cohort 2B-6 50 mg/minute
Cohort 2B-7 60 mg/minute
Cohort 2B-8 70 mg/minute
Cohort 2B-9 80 mg/minute
Cohort 2B-10 90 mg/minute
Cohort 2B-11 100 mg/minute (volume of a full standard vial of EXPAREL® administered in 2.66 minutes)

If 6/12 patients in any cohort report one or more early CNS toxicity symptoms, Part 2B will be stopped and the rate of the previous cohort will be considered the maximum tolerated rate. If <6/12 patients in all cohorts report any symptom, the fastest rate may be utilized in Part 3 of the study.

After each cohort, data will be reviewed by a safety review committee (SRC) who will determine whether to escalate to the next cohort.

Study Part 3: Double-Blind Comparison of Selected Bupivacaine Dose Vs. Selected EXPAREL® Dose The data from Study Parts 1 and 2 will be analyzed, and the most clinically relevant comparison (dose and rate of administration for each drug) will be selected. Part 3 will be a randomized, double-blind comparison between two study arms consisting of 20 patients each:

Arm 1: Bupivacaine (dose and rate TBD)
Arm 2: EXPAREL® (dose and rate TBD)

Each subject's infusion will continue until one of the following occurs:

Subject reports one or more early CNS toxicity symptoms
The full allotted dose of study drug is administered Study injectors will be unblinded as to treatment allocation due to distinguishable differences between treatments (both volume and color). Other study staff (observers, assessors, etc.) will be blinded.

Outcome measures will include the following for EXPAREL® vs. bupivacaine:

Time of onset, frequency and severity of reported symptoms of early CNS toxicity
Frequency and severity of other reported adverse events
Pharmacokinetic measurements
ECG measurements, etc.

* The team might consider infusing drug into lower extremities as opposed to the arm, for the following reasons:
 1. Injecting drug in a lower extremity (below the liver) might lead to a hepatic effect. It is possible that one would see a greater differentiation between EXPAREL® and bupivacaine due to differences in hepatic effects on the two drugs.
 2. Study results would be more readily clinically applicable to lower extremity nerve blocks, in accordance with EXPAREL®'s common clinical use in knee injections. However the results would be less readily applicable to brachial plexus nerve blocks.

Example 2

The following is a summary of the results from two pre-clinical studies that compared the tolerability and PK profiles for non-liposomal bupivacaine vs EXPAREL®

EXPAREL® was better tolerated than free bupivacaine in the form of the hydrochloride salt following intravenous administration in rats and dogs. Improved toleration was attributed to the reduced peak plasma levels of bupivacaine observed in animals following administration of EXPAREL® vs non-liposomal bupivacaine.

1) Intravenous (IV) Administration to Rats of (a) Bupivacaine and (b) EXPAREL®:

Free bupivacaine was administered to three rats in an amount equivalent to 1.0, 1.75 and 2.5 mg/kg of bupivacaine. Two rats died, corresponding to a 67% mortality rate. In a separate experiment, EXPAREL® was administered to rats in an amount equivalent to 2.5, 5.0 and 7.5 mg/kg of bupivacaine. No clinical effects were observed. The NOELs (no observable effect levels) determined for EXPAREL® and for free bupivacaine in this study were 7.5 mg/kg and 1.0 mg/kg, respectively.

Without wishing to be held to any particular mechanism or theory, it is believed that the substantially higher NOEL for EXPAREL® is related to lower intravascular levels (e.g., Cmax) of bupivacaine following administration of EXPAREL® relative to the intravascular levels of bupivacaine following administration of free bupivacaine.

2)

a) Intravenous (IV) Administration to Beagle Dogs of (a) Bupivacaine and (b) EXPAREL®:

Free bupivacaine was administered to dogs in an amount equivalent to 0.75 mg/kg and to 1.5 mg/kg of bupivacaine. Three dogs (one that was administered 0.75 mg/kg, and two that were administered 1.5 mg/kg) experienced side-effects such as convulsions, tremors, increased respiration and/or emesis (Table 1). In a separate experiment, EXPAREL® was administered to dogs in the same amount as above. No adverse effects were observed. A 3-fold higher dose of EXPAREL® (that is, a dose equivalent to 4.5 mg/kg of bupivacaine) was then administered to the dogs. Only one dog experienced side effects (vomiting).

Without wishing to be held to any particular mechanism or theory, it is believed that the observed toxicity differences above are attributable to the differences in plasma bupivacaine levels of the groups of dogs receiving free bupivacaine and EXPAREL®, respectively. In particular, the Cmax for dogs receiving 4.5 mg/kg EXPAREL® was lower than the Cmax for dogs receiving 1.5 mg/kg free bupivacaineK. In particular, the Cmax values following administration of (i) 1.5 mg/kg bupivacaine HCl were 2050 ng/mL and 2750 ng/mL for female and male dogs, respectively; in contrast, the Cmax values following administration of (ii) 4.5 mg/kg of EXPAREL®—i.e., three time the dose of (i)—were 1760 ng/mL and 1810 ng/mL for female and male dogs, respectively. Similarly, the Cmax for dogs receiving the same dose as in (i)—i.e., (1.5 mg/kg) of EXPAREL®—was clearly lower than that of dogs receiving free bupivacaine. In particular, the Cmax values at this dose were 782 ng/mL and 1510 ng/mL for female and male dogs, respectively. The difference in exposure between the two groups may also be seen by comparing the respective values of Cmax/dose. The Cmax/dose was 520 ngxkg/mL/mg and 390 ngxkg/mL/mg for female dogs receiving the 1.5 and 4.5 mg/kg doses of EXPAREL®, respectively, and it was 1,000 ngxkg/mL/mg and 402 ngxkg/mL/mg for male dogs receiving the 1.5 and 4.5 mg/kg doses of EXPAREL®, respectively. The Cmax/dose was 1.37 for female dogs, and 1.83 for male dogs, receiving the 1.5 mg/kg dose of free bupivacaine. In contrast with the above differences in Cmax in the two groups, the total AUC/dose was similar in dogs receiving EXPAREL® as compared to dogs receiving free bupivacaine. In particular, the values for female dogs were 751 (ng-hr/mL)/(mg/kg) for EXPAREL® (1.5 mg/kg dose), 674 (ng-hr/mL)/(mg/kg) for EXPAREL® (4.5 mg/kg dose), and 738 (ng-hr/mL)/(mg/kg)) for free bupivacaine. The values for male dogs were 1510 (ng-hr/mL)/(mg/kg) for EXPAREL® (1.5 mg/kg dose), 826 (ng-hr/mL)/(mg/kg) for EXPAREL® (4.5 mg/kg dose), and 879 (ng-hr/mL)/(mg/kg) for free bupivacaine.

Without wishing to be held to any particular mechanism or theory, it is also believed that the decrease in Cmax observed in dogs receiving EXPAREL® is attributed to sequestration of EXPAREL® particles within animal tissues without causing embolism.

TABLE 1

Comparison of observed adverse events in dogs following intravenous administration of free bupivacaine ("Bupi" in the table) vs EXPAREL ® ("EXP").
Beagle dog study

| Group No. | 1 | 2 | 3 | 4 |
|---|---|---|---|---|
| Formulation | Saline | Bupi | EXP | EXP |
| Dose (mg/kg) | 0 | 0.75, 1.5 | 1.5 | 4.5 |
| | | No. of animals exhibiting clinical symptoms | | |
| Unsustained convulsions | 0 | 0 | 0 | 0 |
| Sustained convulsions | 0 | 1 | 0 | 0 |
| Tremors | 0 | 1 | 0 | 0 |
| Increased respiration | 0 | 2 | 0 | 0 |
| Vomiting | 1 | 2 | 0 | 1 |
| | | Cardiology | | |
| Change in systolic heart rate (mmHg, avg ± SD) | 48 ± 19 | 47 ± 19 | 54 ± 20 | 46 ± 17 |
| Change in heart rate (BMP, avg) | 56 ± 36 | 56 ± 31 | 68 ± 26 | 79 ± 13 |
| ECG | a, b, c, d* | a, b, c, d* | a, b, c, d* | a, b, c, d* |

*(a) Changes consistent with control group; (b) No notable effects on ECG intervals; (c) Highly variable; (d) Secondary to heart rate variability b) Intra-Arterial Administration to Beagle Dogs of (a) Bupivacaine and (b) EXPAREL®:

The study was conducted in a manner analogous to the intravenous administration study described in a) above. The PK parameters from both studies are shown in Table 2 below.

TABLE 2

Mean bupivacaine pharmacokinetic parameters following administration of IA (intra-arterial) or IV (intravenous) administration of bupivacaine or EXPAREL ®.
Summary Mean Bupivacaine Pharmacokinetic Parameters in Female and Male Beagle Dog Plasma Following 0.1 mg/kg, 1.5 mg/kg, and 4.5 mg/kg IV Bolus or Intra-arterial (IA) Administration of Bupivacaine and EXPAREL ® on Day 1

| Formulation | Dose (mg/kg) | Sex | $C_{max}$ (ng/mL) | $C_{max}/D$ (ng · kg/mL/mg) | $AUC_{(0-t)}$ (ng · hr/mL) | $AUC_{(0-t)}/D$ (ng · hr/mL/mg/kg) | $T_{1/2}$ (hr) |
|---|---|---|---|---|---|---|---|
| Bupivacaine (IA) | 0.1 | Female | 187 | 1870 | 62.6 | 626 | 0.267 |
| | | Male | 205 | 2050 | 71.1 | 711 | 0.264 |
| Bupivacaine (IV) | 1.5 | Female | 2050 | 1370 | 1110 | 738 | 0.473 |
| | | Male | 2750 | 1830 | 1320 | 879 | 0.520 |

TABLE 2-continued

Mean bupivacaine pharmacokinetic parameters following administration of IA (intra-arterial) or IV (intravenous) administration of bupivacaine or EXPAREL ®.
Summary Mean Bupivacaine Pharmacokinetic Parameters in Female and Male Beagle Dog Plasma Following 0.1 mg/kg, 1.5 mg/kg, and 4.5 mg/kg IV Bolus or Intra-arterial (IA) Administration of Bupivacaine and EXPAREL ® on Day 1

| Formulation | Dose (mg/kg) | Sex | $C_{max}$ (ng/mL) | $C_{max}/D$ (ng · kg/mL/mg) | $AUC_{(0-t)}$ (ng · hr/mL) | $AUC_{(0-t)}/D$ (ng · hr/mL/mg/kg) | $T_{1/2}$ (hr) |
|---|---|---|---|---|---|---|---|
| EXPAREL ® (IA) | 1.5 | Female | 1950 | 1300 | 1590 | 1060 | 0.471 |
| | | Male | 2070 | 1380 | 1740 | 1160 | 0.539 |
| | 4.5 | Female | 3410 | 758 | 3560 | 791 | 0.744 |
| | | Male | 5400 | 1200 | 7450 | 1650 | 0.787 |
| EXPAREL ® (IV) | 1.5 | Female | 782 | 521 | 1130 | 751 | 1.11 |
| | | Male | 1510 | 1000 | 2260 | 1510 | 0.800 |
| | 4.5 | Female | 1760 | 390 | 3030 | 674 | 0.839 |
| | | Male | 1810 | 402 | 3720 | 826 | 1.06 |

The invention claimed is:

1. A method of treating pain in a subject, the method comprising:
   (A) administering, at a rate of at least 12.5 mg/min and less than 2 cm from a wound in the subject a pharmaceutical composition comprising multivesicular liposomes encapsulating bupivacaine phosphate, said multivesicular liposomes comprising
   bupivacaine or a salt thereof;
   phosphoric acid;
   a lipid component comprising at least one amphipathic lipid and at least one neutral lipid lacking a hydrophilic head group; and,
   optionally, a cholesterol and/or a plant sterol;
   wherein said multivesicular liposomes are made by a process comprising:
   a) preparing a first aqueous component comprising phosphoric acid;
   b) preparing a lipid component comprising at least one organic solvent, at least one amphipathic lipid, and at least one neutral lipid lacking a hydrophilic head group;
   c) mixing said first aqueous component and said lipid component to form a water-in-oil emulsion, wherein at least one component comprises bupivacaine or a salt thereof;
   d) mixing said water-in-oil emulsion with a second aqueous component to form solvent spherules; and
   e) removing the organic solvent from the solvent spherules to form multivesicular liposomes encapsulating bupivacaine phosphate;
   (B) determining that inadvertent administration of the pharmaceutical composition into the vasculature of the subject has occurred;
   (C) monitoring the subject for cardiac side effects and CNS side effects; and
   (D) if cardiac side effects and CNS side effects are absent in the subject, administering into the subject in an additional time period, which is the same or different as the first time period, less than 2 cm from a wound an additional amount of the pharmaceutical composition to the subject, wherein the additional amount is the same as or greater than the amount in step (A).

2. A method of treating pain in a subject, the method comprising (A) administering, at a rate of at least 12.5 mg/min and less than 2 cm from a wound in the subject a pharmaceutical composition comprising a multivesicular liposome comprising bupivacaine phosphate; a lipid component comprising at least one amphipathic lipid and at least one neutral lipid lacking a hydrophilic head group; and, optionally, a cholesterol and/or a plant sterol,
   (B) determining that inadvertent administration of the pharmaceutical composition into the vasculature of the subject has occurred;
   (C) monitoring the subject for cardiac side effects and CNS side effects; and
   (D) if cardiac side effects and CNS side effects are absent in the subject, administering into the subject an additional amount of the pharmaceutical composition the same as or greater than the amount administered less than 2 cm from a wound in the subject.

3. The method of claim 1, wherein the aqueous phase further comprises hydrochloric acid.

4. The method of claim 1, wherein the amphipathic lipid is selected from the group consisting of phosphatidylcholines, phosphatidylethanolamines, sphingomyelins, lysophosphatidylcholines, lysophosphatidylethanolamines, phosphatidylglycerols, phosphatidylserines, phosphatidylinositols, phosphatidic acids, cardiolipins, diacyl dimethylammonium propanes, and stearylamines.

5. The method of claim 1, wherein the neutral lipid is at least one triglyceride.

6. The method of claim 1, wherein the pharmaceutical composition comprises a therapeutically effective amount of bupivacaine phosphate.

7. The method of claim 6, wherein the pharmaceutical composition is present in an amount equivalent to from about 10 mg to about 70 mg of bupivacaine.

8. The method of claim 1, wherein the method comprises administering an opioid to the subject following the administration of the pharmaceutical composition into the subject.

9. The method of claim 8, wherein the opioid is oxycodone and the method comprises administering oxycodone in a total amount less than or equal to 10 mg or administering morphine in a total amount less than or equal to 15 mg in the first about 72 hours following the administration of the pharmaceutical composition.

10. The method of claim 1, wherein the method comprises administering a non-opioid analgesic to the subject following the administration of the pharmaceutical composition into the subject.

11. The method of claim 1, wherein the subject has an AUC for VAS pain intensity scores over the first 72 hours following the administration of the pharmaceutical composition into the subject of from about 100 to about 200.

12. The method of claim 1, wherein the subject has a distress from itchiness score as determined by the OBAS scale of less than 4 following the administration of the pharmaceutical composition into the subject.

13. A method of treating pain in a subject, the method comprising:
(A) administering, at a rate of at least 12.5 mg/min and less than 2 cm from a wound in the subject
a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol;
wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
wherein inadvertent administration of the pharmaceutical composition into the vasculature of the subject provides a plasma Cmax of bupivacaine that is lower than the plasma Cmax of bupivacaine in the subject that would result from administration of an amount of non-liposomal bupivacaine equivalent to the same amount of bupivacaine as the amount of the pharmaceutical composition into the vasculature of the subject;
(B) determining that inadvertent administration of the pharmaceutical composition into the vasculature of the subject has occurred;
(C) monitoring the subject for cardiac side effects and CNS side effects; and
(D) if cardiac side effects and CNS side effects are absent in the subject, administering an additional amount of the pharmaceutical composition, wherein the additional amount is the same as or greater than the amount administered in step (A).

14. A method of treating pain in a subject, the method comprising:
A) administering in a first time period at a rate of at least 12.5 mg/min and less than 2 cm from a wound in the subject an amount of
a pharmaceutical composition comprising multivesicular liposomes encapsulating bupivacaine phosphate, said multivesicular liposomes comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol;
wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate;
B) monitoring the plasma level of bupivacaine in the subject; and
C) if cardiac side effects and CNS side effects are absent in the subject, administering an additional amount of the pharmaceutical composition, wherein the additional amount is the same as or greater than the amount administered in step (A).

15. The method of claim 14, wherein the pharmaceutical composition is administered in an amount equivalent to up to 266 mg of bupivacaine.

16. The method of claim 14, further comprising:
determining that the plasma level of bupivacaine in the subject at a time point following the first administration of the pharmaceutical composition is less than 2,000 ng/mL.

17. The method of claim 1, wherein the subject is a human.

18. The method of claim 1, wherein the plasma level of bupivacaine in the subject at a time point following the administering of the pharmaceutical composition is from about 2 times to about 4 times less than the plasma level of bupivacaine in the subject at the same time point that would result from administration to the subject of the non-liposomal bupivacaine.

19. The method of claim 1, wherein the plasma level of bupivacaine in the subject at a time point following the administering of the pharmaceutical composition is at least 2 times less than the plasma level of bupivacaine in the subject at the same time point that would result from administration to the subject of the non-liposomal bupivacaine.

20. The method of claim 12, wherein the subject has a distress from itchiness score as determined by the OBAS scale of 2 following the administration of the pharmaceutical composition into the subject.

21. The method of claim 12, wherein the subject has a distress from itchiness score as determined by the OBAS scale of 1 following the administration of the pharmaceutical composition into the subject.

22. The method of claim 12, wherein the subject has a distress from itchiness score as determined by the OBAS scale of 0 following the administration of the pharmaceutical composition into the subject.

23. The method of claim 1, wherein the rate of at least 12.5 mg/min is between 12.5 mg/min and 100 mg/min.

24. The method of claim 2, wherein the rate of at least 12.5 mg/min is between 12.5 mg/min and 100 mg/min.

25. The method of claim 13, wherein the rate of at least 12.5 mg/min is between 12.5 mg/min and 100 mg/min.

26. The method of claim 1, wherein the pharmaceutical composition is administered at a rate selected from the group consisting of: 15 mg/minute, 20 mg/minute, 30 mg/minute, 40 mg/minute, 50 mg/minute, 60 mg/minute, 70 mg/minute, 80 mg/minute, 90 mg/minute, and 100 mg/minute.

27. The method of claim 2, wherein the pharmaceutical composition is administered at a rate selected from the group consisting of: 15 mg/minute, 20 mg/minute, 30 mg/minute, 40 mg/minute, 50 mg/minute, 60 mg/minute, 70 mg/minute, 80 mg/minute, 90 mg/minute, and 100 mg/minute.

28. The method of claim 13, wherein the pharmaceutical composition is administered at a rate selected from the group consisting of: 15 mg/minute, 20 mg/minute, 30 mg/minute, 40 mg/minute, 50 mg/minute, 60 mg/minute, 70 mg/minute, 80 mg/minute, 90 mg/minute, and 100 mg/minute.

29. The method of claim 14, wherein the pharmaceutical composition is administered at a rate selected from the group consisting of: 15 mg/minute, 20 mg/minute, 30 mg/minute, 40 mg/minute, 50 mg/minute, 60 mg/minute, 70 mg/minute, 80 mg/minute, 90 mg/minute, and 100 mg/minute.

30. The method of claim 14, wherein the rate of at least 12.5 mg/min is between 12.5 mg/min and 100 mg/min.

\* \* \* \* \*